(12) United States Patent
Irvin et al.

(10) Patent No.: US 6,767,545 B2
(45) Date of Patent: Jul. 27, 2004

(54) PSEUDOMONAS TREATMENT COMPOSITION AND METHOD

(75) Inventors: Randall T. Irvin, Sherwood Park (CA); Randy J. Read, Cambridge (GB); Bart Hazes, Edmonton (CA); Wah Y. Wong, Edmonton (CA); Sastry A. Parimi, deceased, late of Edmonton (CA), by Sastry A. Parimi, legal representative; Linda M. G. Glasier, Edmonton (CA)

(73) Assignee: Governors of the University of Alberta, Edmonton (CA)

( * ) Notice: Subject to any disclaimer, the term of this patent is extended or adjusted under 35 U.S.C. 154(b) by 0 days.

(21) Appl. No.: 09/865,159

(22) Filed: May 24, 2001

(65) Prior Publication Data

US 2002/0098196 A1 Jul. 25, 2002

Related U.S. Application Data

(63) Continuation of application No. 09/329,884, filed on Jun. 11, 1999, now Pat. No. 6,342,233.
(60) Provisional application No. 60/089,155, filed on Jun. 12, 1998.

(51) Int. Cl.$^7$ ................................................. A61K 39/02
(52) U.S. Cl. ................................. 424/260.1; 424/185.1; 424/190.1; 424/242.1; 530/350
(58) Field of Search ........................... 424/260.1, 185.1, 424/190.1, 242.1; 530/350

(56) References Cited

U.S. PATENT DOCUMENTS

| | | | |
|---|---|---|---|
| 5,445,818 | A | 8/1995 | Hodges et al. |
| 5,468,484 | A | 11/1995 | Hodges et al. |
| 5,494,672 | A | 2/1996 | Hodges et al. |
| 5,612,036 | A | 3/1997 | Hodges et al. |

FOREIGN PATENT DOCUMENTS

| | | |
|---|---|---|
| WO | WO 90/11777 | 10/1990 |
| WO | WO 95/31480 | 11/1995 |
| WO | WO 97/12988 | 4/1997 |
| WO | WO 98/52976 | 11/1998 |

OTHER PUBLICATIONS

Irvin, R.T. (1993) "Attachment and Colonization of *Pseudomonas aeruginosa*: Role of the surface Structures", pp 19–42, Plenum Press, New York.
Pier, G.B., (1985) "Pulmonary Disease Associated with *Pseudomonas aeruginosa* in Cystic Fibrosis: Current Status of the Host–Bacterium Interaction", J. Infect. Dis. 151:575–580.
Rivera, M., et al. (1982) "*Pseudomonas aeruginosa* Mucoid Strain", Am. Rev. Respir. Dis. 126:833–836.

Todd, T.R.J., et al. (1989) "Augmented Bacterial Adherence to Tracheal Epithelial Cells Is Associated with Gram–Negative Pneumonia in an Intensive Care Unit Population", Am. Rev. Respir. Dis. 140:1585–1589.
Irvin, R.T., et al. (1989) "Characterization of the *Pseudomonas aeruginosa* Pilus Adhesin: Confirmation that the Pilin Structural Protein Subunit Contains a Human Epithelial Cell–Binding Domain", Infect. Immun. 57:3720–3726.
Lee, K.K., et al. (1989) "Mapping the surface regions of *Pseudomonas aeruginosa* PAK pilin: the importance of the C–terminal region for adherence to human buccal epithelial cells," Mol. Microbial. 3:1493–1499.
Doig, P., et al. (1987) "Characterization of the Binding of *Pseudomonas aeruginosa* Alginate to Human Epithelial Cells," Infect. Immun. 55:1517–1522.
Irvin, R.T., et al. (1990) "Usefulness of Equilibrium Parameters of Adhesion in Predicting the Outcome of Competition for Bacterial Receptor Sites on Respiratory Epithelial Cells by *Pseudomonas aeruginosa* Strains of Heterologous Pilus Type", Microb. Ecol. Health Dis. 3:39–47.
Bradley, D.E. (1972) "A study of pili on *Pseudomonas aeruginosa*", Genet. Res. 19:39–51.
Folkhard, W.F., et al. (1981) "Structure of Polar Pili from *Pseudomonas aeruginosa* Strains K and O", J. Mol. Biol. 149:79–93.
Paranchych, W., et al. (1986) "Fimbriae (Pili): Molecular Basis of *Pseudomonas aeruginosa* Adherence", Clin Invest Med 9:113–118.
Paranchych, W., et al. (1990) "Expression, processing, and assembly of *Pseudomonas aeruginosa* N–methylphenylalanine pilin", in *Pseudomonas: Biotransformations, Pathogenesis and Evolving Biotechnology*, (Sliver, S., et al., eds.), pp 343–351, American Society for Microbiology, Washington, D.C.
Pasloske, B. L., et al. (1988) "Two Unusual Pilin Sequences from Different Isolates of *Pseudomonas aeruginosa*", J. Bacteriol. 170:3738–3741.
Yu, L., et al. (1994) "Adherence of *Pseudomonas aeruginosa* and *Candida albicans* to Glycosphingolipid (Asialo–$GM_1$) Receptors Is Achieved by a Conserved Receptor–Binding Domain Present on Their Adhesins", Infect. Immun. 62:5213–9.
Sheth, H.B., et al. (1994) "The pili of *Pseudomonas aeruginosa* strains PAK and PAO bind specifically to the carbohydrate sequence $\beta$GalNAc(1–4)$\beta$Gal found in glycosphingolipids asialo–$GM_1$ and asialo–$GM_2$", Mol. Microbiol. 11:715–23.

(List continued on next page.)

Primary Examiner—Jennifer E. Graser
(74) Attorney, Agent, or Firm—Bell, Boyd & Lloyd LLC

(57) ABSTRACT

A composition and method for treating or preventing infection by *Pseudomonas aeruginosa* is disclosed. The composition includes a *P. aeruginosa* pilin peptide modified to prevent oligomerization of the pilin. The method involves administered the composition to a person infected with Pseudomonas are at risk of such infection.

1 Claim, 13 Drawing Sheets

OTHER PUBLICATIONS

Figure 2A:
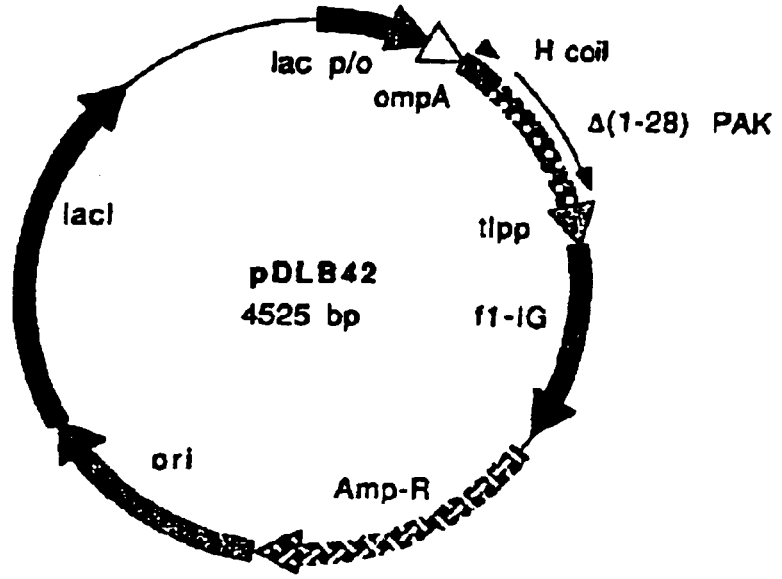

Doig, P., et al. (1990) "Inhibition of Pilus–Mediated Adhesion of *Pseudomonas aeruginosa* to Human Buccal Epithelial Cells by Monoclonal Antibodies Directed against Pili", *Infect. Immun.* 58:124–130.

Lee, K.K., et al. (1989) "Immunological Studies of the Disulfide Bridge Region of *Pseudomonas aeruginosa* PAK and PAO Pilins, Using Anti–PAK Pilus and Antipeptide Antibodies", *Infect. Immun.* 57:520–526.

Sheth, H.B., et al. (1995) "Development of an anti–adhesive vaccine for *Pseudomonas aeruginosa* targeting the C–terminal region of the pilin structural protein", *Biomed. Pept. Proteins and Nucleic Acids* 1:141–148.

Spangenberg, C., et al. (1995) "Comparison of type IV–pilin genes of *Pseudomononas aeruginosa* of various habitats has uncovered a novel unusual sequence", *FEMS Microbiol Lett* 125:(2–3):265–273.

Koga, T., et al. (1993) "Genetic and functional characterization of the gene cluster specifying expression of *Pseudomonas aeruginosa* pili", *Infect Immunol* 61(4):1371–1377.

Sastry, P.A., et al. (1985) "Comparative studies of the amino acid and nucleotide sequences of pilin derived from *Pseudomonas aeruginosa* PAK and PAO", *J. Bacteriol.* 164(2):571–577.

Johnson, K., et al. (1986) "Nucleotide sequence and transcriptional initiation site of two *Pseudomonas aeruginosa* pilin genes", *J. Biol Chem.* 261(33):15703–15708.

Castric, P.A., et al. (1989) "Cloning and sequencing of the *Pseudomonas aeruginosa* 1244 pilin structural gene", *Mol Gen Genet* 216(1):75–80.

Strom, M.S., et al. (1986) "Cloning and expression of the pilin gene of *Pseudomonas aeruginosa* PAK in *Escherichia coli*", *J. Bacteriol.* 165(2):367–372.

Yi, T.M., et al. (1993) "Protein secondary structure prediction using nearest–neighbor methods", *J Mol Biol.* 232(4):1117–1129.

Viswanadhan, V.N., et al. (1991) "New joint prediction algorithm ($Q_7$–JASEP) improves the prediction of protein secondary structure", *Biochemistry* 30(46):11164–11172.

King, R.D., et al. (1990) "Machine learning approach for the prediction of protein secondary structure", *J Mol Biol* 216(2):441–457.

Biou V., et al. (1988) "Secondary structure prediction: combination of three different methods", *Protein Eng* 2(3):185–191.

Corrigan, A.J. (1982) "A Basic microcomputer program for plotting the secondary structure of proteins", *Comput Programs Biomed.* 15(3):163–168.

Tripet, B.L., et al. (1996) "Engineering a de novo–designed coiled–coil heterodimerization domain for the rapid detection, purification and characterization of recombinantly expressed peptides and proteins", *Protein Eng* 9:1029–1042.

Chao, H., et al. (1998) "Use of a heterodimeric coiled–soil system for biosensor application and affinity purification", *J. Chrom A.* 715:307–329.

Zhou N.E., et al. (1993) "A single–stranded amphipathic α–helix in aqueous solution: design, structural characterization, and its application for determining α–helical propensities of amino acids", *Biochemistry* 32:6190–6197.

Gunasekaran, K., et al. (1998) "Stereochemical Punctuation Marks in Protein Structures: Glycine and Proline Containing Helix Stop Signals", *J Mol Biol* 6:917–932.

Paranchych, W., et al. (1988) "The physiology and biochemistry of pili", *Advan Microbiol Phys* 29:53–114.

Paranchych, W., et al. (1979) "Biochemical studies on pili isolated from *Pseudonomas aeruginosa* strain PAO", *Can J. Microbiol* 25:1175–1181.

Pasloske B.L., et al. (1988) "The expression of mutant pilins in *Pseudomonas aeruginosa*: fifth position glutamate affects pilin methylation", *Mol Microbiol* 2:489–495.

Pasloske, B.L., et al. (1985) "Cloning and sequencing of the *Pseudomonas aeruginosa* PAK pilin gene", *FEBS Lets* 183:408–412.

Campbell et al, NMR solution structure of the receptor binding domain of *Pseudomonas aeruginosa* pilin strain P1; Int. J. Peptide Protein Res.; vol. 48, pp. 539–552 (1996).

Tripet et al, Engineering a de novo designed coiled–coil heterodimerization domain for the rapid detection, purification and characterization of recombinantly expressed peptides and proteins; Protein Engineering; vol. 9, No. 11; pp. 1029–1042 (1996).

```
1/1
GCG CTC GAG GGT ACC GAA TTC GCA CGC GCT CTT AGC GAA CGC ATG ACC CTG GCC AGT
 A   L   E   G   T   E   F   A   R   A   L   S   E   R   M   T   L   A   S
61/21                                                           31/11
GGT CTC AAG ACG GCA AAA GTG AGC GAT ATC TTC TCT CAG GAT GGG TCC TGC CCG GCT AAT ACT
 G   L   K   T   A   K   V   S   D   I   F   S   Q   D   G   S   C   P   A   N   T
121/41                                                          91/31
GCT GCC ACG GCA GGC ATC GAG AAA GAT ACC AAC GGC AAG TAT GTT GCC ACT ATG AAA GCC
 A   A   T   A   G   I   E   K   D   T   N   G   K   Y   V   A   T   M   K   A
181/61                                                          151/51
ACA ACT GGT GGC ACC GCA CCT CTG AGG GGG AAA ACT CTG ACT ATC GTT ACT CTA GGA AAT GCT GAC
 T   T   G   G   T   A   P   L   R   G   K   T   L   T   I   V   T   L   G   N   A   D
241/81                                                          211/71
TCT GAT GTG GCT ACT CCT CTG TGG GCC TGT ACT TCC AAC GGC GAT AAC AAG TAC CTG CCA AAA ACC
 S   D   V   A   T   P   L   W   A   C   T   S   N   G   D   N   K   Y   L   P   K   T
301/101                                                         271/91
AAG GGT TCT TAC ACT TGG GCC TGT ACT TCC AAC GCA GAT AAC AAG TAC CTG CCA AAA ACC
 K   G   S   Y   T   W   A   C   T   S   N   A   D   N   K   Y   L   P   K   T
361/121                                                         331/111
TGC CAG ACT GCT ACC ACT CCG
 C   Q   T   A   T   T   P
```

Fig. 1A

```
1/1
GCG CTC GAG GGT ACC GAA TTC GCT CGT TCG GAA GGC GCA TCT GCT CTT GCT TCG GTC AAT
 A   L   E   G   T   E   F   A   R   S   E   G   A   S   A   L   A   S   V   N
61/21                                                                       31/11
CCG TTG AAG ACT ACC GTT GAA GAG GCG CTT TCT CGT GGT TGG AGC GTG AAG AGC GGT ACA
 P   L   K   T   T   V   E   E   A   L   S   R   G   W   S   V   K   S   G   T
121/41                                                                      91/31
GGT ACA GAG GAC GCT ACT AAG AAA GAG GTT CCT CTG GGG GTG GCG GCA GAT GCT AAC AAA
 G   T   E   D   A   T   K   K   E   V   P   L   G   V   A   A   D   A   N   K
181/61                                                                     151/51
CTG GGT ACT ATC GCA CTC AAA CCC GAT CCT GCT GAT GGT ACT GCA GAT ATC ACT TTG ACT
 L   G   T   I   A   L   K   P   D   P   A   D   G   T   A   D   I   T   L   T
241/81                                                                     211/71
TTC ACT ATG GGC GGT GCA GGA CCG AAG AAT AAA GGG AAA ATT ATT ACC CTG ACT CGT ACT
 F   T   M   G   G   A   G   P   K   N   K   G   K   I   I   T   L   T   R   T
301/101                                                                    271/91
GCA GCT GAT GGT CTC TGG AAG TGC ACC AGT GAT GAT CAG GAT GAG CAG TTT ATT CCG AAA GGT
 A   A   D   G   L   W   K   C   T   S   D   D   Q   D   E   Q   F   I   P   K   G
361/121                                                                    331/111
TGC TCT AGG
 C   S   R

Fig. 1B
```

```
1/1
GCG CTC GAG GGT ACC GAA TTC GCG CGT TCG                             31/11
 A   L   E   G   T   E   F   A   R   S   GAA GGT GCT TCG GCG CTG GCG ACG ATC AAC
61/21                                      E   G   A   S   A   L   A   T   I   N
CCG CTG AAG ACC ACT GTT GAA GAG TCG CTG                             91/31
 P   L   K   T   T   V   E   E   S   L   TCG CGT GGA ATT GCT GGT AGC AAA ATT AAA
121/41                                     S   R   G   I   A   G   S   K   I   K
ATT GGT ACT ACT GCT TCT ACT GCG ACC GAA                            151/51
 I   G   T   T   A   S   T   A   T   E   ACA TAT GCC GGC GTC GAG CCG GAT GCC AAC
181/61                                     T   Y   A   G   V   E   P   D   A   N
AAG TTG GGT GTA ATT GCT GTA GCA ATC GAA                            211/71
 K   L   G   V   I   A   V   A   I   E   GAT AGT GGT GCG GGT GAT ATT ACT CTG ACT
241/81                                     D   S   G   A   G   D   I   T   L   T
TTC CAG ACT GGT ACC TCT AGT CCC AAG AAT                            271/91
 F   Q   T   G   T   S   S   P   K   N   GCT ACT AAA GTT ATC ACT AAC CGT ACT
301/101                                    A   T   K   V   I   T   N   R   T
GCG GAT GGG GTC TGG GCT TGT AAA TCT ACC                            331/111
 A   D   G   V   W   A   C   K   S   T   CAG GAT CCG ATG TTC ACT CCG AAA GGT T̂ÊT
361/121                                    Q   D   P   M   F   T   P   K   G  S
GAT AAC
 D   N
```

Fig. 1C

1/1
GCG CTC GAG GGT ACC GAA TTC GCC CGT ACC CAG GTG ACC CGT GCC GTG AGT GAA GTC AGC
A   L   E   G   T   E   F   A   R   T   Q   V   T   R   A   V   S   E   V   S
                                    31/11
61/21
GCG CTG AAG ACC GCT GCG GAG TCG GCG ATT CTG GAA GGG AAG GAG ATT GTT TCC AGC GCG
A   L   K   T   A   A   E   S   A   I   L   E   G   K   E   I   V   S   S   A
                                    91/31
121/41
ACT CCT AAA GAT ACC CAG TAT GAC ATT GGC TTC ACC GAG TCT ACT TTG CTA GAT GGT TCT
T   P   K   D   T   Q   Y   D   I   G   F   T   E   S   T   L   L   D   G   S
                                    151/51
181/61
GGT AAG AGT CAG ATC CAG GTA ACG GAC AAT AAA GAT GGC ACC GTT GAG TTG GTC GCT ACC
G   K   S   Q   I   Q   V   T   D   N   K   D   G   T   V   E   L   V   A   T
                                    211/71
241/81
TTG GGT AAA TCT TCT GGT TCC GCC ATC AAA ACC AAA GGG GCT GTA ATC ACT GTT TCG CGT AAA AAT
L   G   K   S   S   G   S   A   I   K   T   K   G   A   V   I   T   V   S   R   K   N
                                    271/91
301/101                                                                 331/111
GAC GGA GTC TGG AAC TGC AAA ATC ACC AAA ATC ACC CCT ACA GCT TGG AAG CCC AAC TAC GCT
D   G   V   W   N   C   K   I   T   K   I   T   P   T   A   W   K   P   N   Y   A
361/121
CCG GCT AAT TGC CCG AAT TCC
P   A   N   C   P   N   S

Fig. 1D

```
1/1
GCG CTC GAG GGT ACC GAA TTC TCT CGC TCT                                 31/11
 A   L   E   G   T   E   F   S   R   S   CAG GTC TCC AGG GTT ATG GCG GAG GCT GGC
                                          Q   V   S   R   V   M   A   E   A   G
61/21                                                                   91/31
TCC TTG AAG ACT GCA GTT GAG GCC TGC CTC   CAG GAT GGT CGT ACT GCT GTG GGT ACT GCT
 S   L   K   T   A   V   E   A   C   L    Q   D   G   R   T   A   V   G   T   A
121/41                                                                  151/51
GCT GGT CAA TGC GAT CCG GGT GCG ACG GGT   TCC AGT TTG ACT GGT GCT TCT CAG ACT
 A   G   Q   C   D   P   G   A   T   G    S   S   L   T   G   A   S   Q   T
181/61                                                                  211/71
TCT CAA ACC CTG CCA ACC AAT ACC GGT GTT   CCG CAG GTT CTG GAT CCT CTG ACT ACT CAA
 S   Q   T   L   P   T   N   T   G   V    P   Q   V   L   D   P   L   T   T   Q
241/81                                                                  271/91
ACC ACT ATC ATT GCG ACT TTT GGT AAC GGC   GCA TCC GCA GCT ATT TCT GGC CAG ACT CTG
 T   T   I   I   A   T   F   G   N   G    A   S   A   A   I   S   G   Q   T   L
301/101                                                                 331/111
ACC TGG ACT CGT GAT GTT AAT GGT GGC TGG   AGC TGT GCT ACT ACC GTA GAT GCT AAA TTC
 T   W   T   R   D   V   N   G   G   W    S   C   A   T   T   V   D   A   K   F
361/121
CGT CCT AAT GGC TGT ACT GAC
 R   P   N   G   C   T   D
```

Fig. 1E

```
DNA sequence    613 b.p.    ttctagataacg ...AAGAAGCTTGGG linear

86/1                                          116/11
gcg ctc gag cac cat cat cac cat ggt ggt ggt ggc gag att gag gcc ctc aag gct gaa
 A   L   E   H   H   H   H   H   G   G   G   G   E   I   E   A   L   K   A   E
146/21                                         176/31
atc gaa gcc cta aag gcc gag ata gaa gca ctt aag gca gag atc gag gcg cta aaa gcg
 I   E   A   L   K   A   E   I   E   A   L   K   A   E   I   E   A   L   K   A
206/41                                         236/51
gaa ata gag gct ctg aag gca ggc ggt gga gga gaa ttc GCT CGT TCG GAA GGC GCA TCT
 E   I   E   A   L   K   A   G   G   G   G   E   F   A   R   S   E   G   A   S
266/61                                         296/71
GCT CTT GCT TCG GTC AAT CCG TTG AAG ACT ACC GTT GAA GAG GCG CTT TCT CGT GGT TGG
 A   L   A   S   V   N   P   L   K   T   T   V   E   E   A   L   S   R   G   W
326/81                                         356/91
AGC CTG AAG AGC GGT ACA GGT ACA GAG GAC GCT ACT AAG AAA GAG GTT CCT CTG GGG GTG
 S   V   K   S   G   T   G   T   E   D   A   T   K   K   E   V   P   L   G   V
386/101                                        416/111
GCG GCA GAT GCT AAC AAA CTG GGT ACT ATC GCA CTC AAA CCC GAT CCT GCT GAT GGT ACT
 A   A   D   A   N   K   L   G   T   I   A   L   K   P   D   P   A   D   G   T
446/121                                        476/131
GCA GAT ATC ACT TTG ACT TTC ACT ATG GGC GGT GCA GGA CCG AAG AAT AAA GGG AAA ATT
 A   D   I   T   L   T   F   T   M   G   G   A   G   P   K   N   K   G   K   I
506/141                                        536/151
ATT ACC CTG ACT CGT ACT GCA GCT GAT GGT CTC TGG AAG TGC ACC AGT GAT CAG GAT GAG
 I   T   L   T   R   T   A   A   D   G   L   W   K   C   T   S   D   Q   D   E
566/161
CAG TTT ATT CCG AAA GGT TGC TCT AGG
 Q   F   I   P   K   G   C   S   R
```

Fig. 3A

```
DNA sequence    613 b.p.    ttctagataacg ... AAGAAGCTTGGG linear

86/1                                          116/11
gcg ctc gag cac cat cat cac cat ggt ggt ggt ggc gag gta tcc gct tta gag aaa gaa
 A   L   E   H   H   H   H   H   G   G   G   G   E   V   S   A   L   E   K   E
146/21                                         176/31
gtt tct gct ctc gaa aaa gag gtc agt gct ctg gaa aaa gag gtg tca gcc ttg gaa aag
 V   S   A   L   E   K   E   V   S   A   L   E   K   E   V   S   A   L   E   K
206/41                                         236/51
gaa gta tca gca ctt gag aag ggc ggt gga gga gaa ttc GCT CGT TCG GAA GGC GCA TCT
 E   V   S   A   L   E   K   G   G   G   G   E   F   A   R   S   E   G   A   S
266/61                                         296/71
GCT CTT GCT TCG GTC AAT CCG TTG AAG ACT ACC GTT GAA GAG GCG CTT TCT CGT GGT TGG
 A   L   A   S   V   N   P   L   K   T   T   V   E   E   A   L   S   R   G   W
326/81                                         356/91
AGC CTG AAG AGC GGT ACA GGT ACA GAG GAC GCT ACT AAG AAA GAG GTT CCT CTG GGG GTG
 S   V   K   S   G   T   G   T   E   D   A   T   K   K   E   V   P   L   G   V
386/101                                        416/111
GCG GCA GAT GCT AAC AAA CTG GGT ACT ATC GCA CTC AAA CCC GAT CCT GCT GAT GGT ACT
 A   A   D   A   N   K   L   G   T   I   A   L   K   P   D   P   A   D   G   T
446/121                                        476/131
GCA GAT ATC ACT TTG ACT TTC ACT ATG GGC GGT GCA GGA CCG AAG AAT AAA GGG AAA ATT
 A   D   I   T   L   T   F   T   M   G   G   A       P   K   N   K   G   K   I
506/141                                        536/151
ATT ACC CTG ACT CGT ACT GCA GCT GAT GGT CTC TGG AAG TGC ACC AGT GAT CAG GAT GAG
 I   T   L   T   R   T   A   A   D   G   L   W   K   C   T   S   D   Q   D   E
566/161
CAG TTT ATT CCG AAA GGT TGC TCT AGG
 Q   F   I   P   K   G   C   S   R
```

Fig. 3B

```
DNA sequence      631 b.p.   ttctagataacg ... AGCAAGCTTGGG  linear

86/1                                          116/11
gcg ctc gag cac cat cat cac cat ggt ggt ggt ggc gag att gag gcc ctc aag gct gaa
 A   L   E   H   H   H   H   H   G   G   G   G   E   I   E   A   L   K   A   E
146/21                                        176/31
atc gaa gcc cta aag gcc gag ata gaa gca ctt aag gca gag atc gag gcg cta aaa gcg
 I   E   A   L   K   A   E   I   E   A   L   K   A   E   I   E   A   L   K   A
206/41                                        236/51
gaa ata gag gct ctg aag gca ggc ggt gga gga gaa ttc GCA CGC GCT CAG CTT AGC GAA
 E   I   E   A   L   K   A   G   G   G   G   E   F   A   R   A   Q   L   S   E
266/61                                        296/71
CGC ATG ACC CTG GCC AGT GGT CTC AAG ACG AAA GTG AGC GAT ATC TTC TCT CAG GAT GGG
 R   M   T   L   A   S   G   L   K   T   K   V   S   D   I   F   S   Q   D   G
326/81                                        356/91
TCC TGC CCG GCT AAT ACT GCT GCC ACG GCA GGC ATC GAG AAA GAT ACC GAC ATC AAC GGC
 S   C   P   A   N   T   A   A   T   A   G   I   E   K   D   T   D   I   N   G
386/101                                       416/111
AAG TAT GTT GCC AAG GTA ACA ACT GGT GGC ACC GCA GCT GCG TCT GGT GGT TGC ACT ATC
 K   Y   V   A   K   V   T   T   G   G   T   A   A   S   G   G   C   T   I
446/121                                       476/131
GTT GCT ACT ATG AAA GCC TCT GAT GTG GCT ACT CCT CTG AGG GGG AAA ACT CTG ACT TTG
 V   A   T   M   K   A   S   D   V   A   T   P   L   R   G   K   T   L   T   L
506/141                                       536/151
ACT CTA GGA AAT GCT GAC AAG GGT TCT TAC ACT TGG GCC TGT ACT TCC AAC GCA GAT AAC
 T   L   G   N   A   D   K   G   S   Y   T   W   A   C   T   S   N   A   D   N
566/161                                       596/171
AAG TAC CTG CCA AAA ACC TGC CAG ACT GCT ACC ACT ACC ACT CCG
 K   Y   L   P   K   T   C   Q   T   A   T   T   T   T   P
```

Fig. 4A

```
DNA sequence      631 b.p.   ttctagataacg ... AGCAAGCTTGGG  linear

86/1                                          116/11
gcg ctc gag cac cat cat cac cat ggt ggt ggt ggc gag gta tcc gct tta gag aaa gaa
 A   L   E   H   H   H   H   H   G   G   G   G   E   V   S   A   L   E   K   E
146/21                                        176/31
gtt tct gct ctc gaa aaa gag gtc agt gct ctg gaa aaa gag gtg tca gcc ttg gaa aag
 V   S   A   L   E   K   E   V   S   A   L   E   K   E   V   S   A   L   E   K
206/41                                        236/51
gaa gta tca gca ctt gag aag ggc ggt gga gga gaa ttc GCA CGC GCT CAG CTT AGC GAA
 E   V   S   A   L   E   K   G   G   G   G   E   F   A   R   A   Q   L   S   E
266/61                                        296/71
CGC ATG ACC CTG GCC AGT GGT CTC AAG ACG AAA GTG AGC GAT ATC TTC TCT CAG GAT GGG
 R   M   T   L   A   S   G   L   K   T   K   V   S   D   I   F   S   Q   D   G
326/81                                        356/91
TCC TGC CCG GCT AAT ACT GCT GCC ACG GCA GGC ATC GAG AAA GAT ACC GAC ATC AAC GGC
 S   C   P   A   N   T   A   A   T   A   G   I   E   K   D   T   D   I   N   G
386/101                                       416/111
AAG TAT GTT GCC AAG GTA ACA ACT GGT GGC ACC CCA GCT GCG TCT GGT GGT TGC ACT ATC
 K   Y   V   A   K   V   T   T   G   G   T   A   A   S   G   G   C   T   I
446/121                                       476/131
GTT GCT ACT ATG AAA GCC TCT GAT GTG GCT ACT CCT CTG AGG GGG AAA ACT CTG ACT TTG
 V   A   T   M   K   A   S   D   V   A   T   P   L   R   G   K   T   L   T   L
506/141                                       536/151
ACT CTA GGA AAT GCT GAC AAG GGT TCT TAC ACT TGG GCC TGT ACT TCC AAC GCA GAT AAC
 T   L   G   N   A   D   K   G   S   Y   T   W   A   C   T   S   N   A   D   N
566/161                                       596/171
AAG TAC CTG CCA AAA ACC TGC CAG ACT GCT ACC ACT ACC ACT CCG
 K   Y   L   P   K   T   C   Q   T   A   T   T   T   T   P
```

Fig. 4B

DNA sequence      610 b.p.    ttctagataacg ... CGAAAOCTTCGG    linear

```
86/1                                                116/11
gcg ctc gag cac cat cat cac cat ggt ggt ggt ggc gag att gag gcc ctc aag gct gaa
 A   L   E   H   H   H   H   H   G   G   G   G   E   I   E   A   L   K   A   E
146/21                                              176/31
atc gaa gcc cta aag gcc gag ata gaa gca ctt aag gca gag atc gag gcg cta aaa gcg
 I   E   A   L   K   A   E   I   E   A   L   K   A   E   I   E   A   L   K   A
206/41                                              236/51
gaa ata gag gct ctg aag gca ggc ggt gga gaa ttc GCG CGT TCG GAA GGT GCT TCG
 E   I   E   A   L   K   A   G   G   G   E   F   A   R   S   E   G   A   S
266/61                                              296/71
GCG CTG GCG ACG ATC AAC CCG CTG AAG ACC ACT GTT GAA GAG TCG CTG TCG CGT GGA ATT
 A   L   A   T   I   N   P   L   K   T   T   V   E   E   S   L   S   R   G   I
326/81                                              356/91
GCT GGT AGC AAA ATT AAA ATT GGT ACT ACT GCT TCT ACT GCG ACC GAA ACA TAT GCC GGC
 A   G   S   K   I   K   I   G   T   T   A   S   T   A   T   E   T   Y   A   G
386/101                                             416/111
GTC GAG CCG GAT GCC AAC AAG TTG GGT GTA ATT GCT GTA GCA ATC GAA GAT AGT GGT GCG
 V   E   P   D   A   N   K   L   G   V   I   A   V   A   I   E   D   S   G   A
446/121                                             476/131
GGT GAT ATT ACC TTT ACC TTC CAG ACT GGT ACC TCT AGT CCC AAG AAT GCT ACT AAA GTT
 G   D   I   T   F   T   F   Q   T   G   T   S   S   P   K   N   A   T   K   V
506/141                                             536/151
ATC ACT CTG AAC CGT ACT GCG GAT GGG GTC TGG GCT TGT AAA TCT ACC CAG GAT CCG ATG
 I   T   L   N   R   T   A   D   G   V   W   A   C   K   S   T   Q   D   P   M
566/161              G
TTC ACT CCG AAA GGT TGT GAT AAC
 F   T   P   K   G   C   D   N
                     C
```

Fig. 5A

DNA sequence      610 b.p.    ttctagataacg ... CGAAAOCTTCGG    linear

```
86/1                                                116/11
gcg ctc gag cac cat cat cac cat ggt ggt ggt ggc gag gta tcc gct tta gag aaa gaa
 A   L   E   H   H   H   H   H   G   G   G   G   E   V   S   A   L   E   K   E
146/21                                              176/31
gtt tct gct ctc gaa aaa gag gtc agt gct ctg gaa aaa gag gtg tca gcc ttg gaa aag
 V   S   A   L   E   K   E   V   S   A   L   E   K   E   V   S   A   L   E   K
206/41                                              236/51
gaa gta tca gca ctt gag aag ggc ggt gga gga gaa ttc GCG CGT TCG GAA GGT GCT TCG
 E   V   S   A   L   E   K   G   G   G   G   E   F   A   R   S   E   G   A   S
266/61                                              296/71
GCG CTG GCG ACG ATC AAC CCG CTG AAG ACC ACT GTT GAA GAG TCG CTG TCG CGT GGA ATT
 A   L   A   T   I   N   P   L   K   T   T   V   E   E   S   L   S   R   G   I
326/81                                              356/91
GCT GGT AGC AAA ATT AAA ATT GGT ACT ACT GCT TCT ACT GCG ACC GAA ACA TAT GCC GGC
 A   G   S   K   I   K   I   G   T   T   A   S   T   A   T   E   T   Y   A   G
386/101                                             416/111
GTC GAG CCG GAT GCC AAC AAG TTG GGT GTA ATT GCT GTA GCA ATC GAA GAT AGT GGT GCG
 V   E   P   D   A   N   K   L   G   V   I   A   V   A   I   E   D   S   G   A
446/121                                             476/131
GGT GAT ATT ACC TTT ACC TTC CAG ACT GGT ACC TCT AGT CCC AAG AAT GCT ACT AAA GTT
 G   D   I   T   F   T   F   Q   T   G   T   S   S   P   K   N   A   T   K   V
506/141                                             536/151
ATC ACT CTG AAC CGT ACT GCG GAT GGG GTC TGG GCT TGT AAA TCT ACC CAG GAT CCG ATG
 I   T   L   N   R   T   A   D   G   V   W   A   C   K   S   T   Q   D   P   M
566/161              G
TTC ACT CCG AAA GGT TGT GAT AAC
 F   T   P   K   G   C   D   N
                     C
```

Fig. 5B

PSEUDOMONAS TREATMENT COMPOSITION AND METHOD

The present application is a continuation of U.S. patent application Ser. No. 09/329,884 filed on Jun. 11, 1999 now U.S. Pat. No. 6,342,233 B1.

This application claims priority to U.S. Provisional Application Serial No. 60/089,155 filed Jun. 12, 1998, which is hereby incorporated by reference.

FIELD OF THE INVENTION

The present invention relates to a novel composition and method for treatment and prevention of infection by *Pseudomonas aeruginosa*.

REFERENCES

1. Irvin, R. T. (1993) "Attachment and colonization of *Pseudomonas aeruginosa*: Role of the surface structures", in *Pseudomonas aeruginosa* as an Opportunistic Pathogen, (Campa, M., M. Bendinelli, and H. Friedman, eds.), pp 1942, Plenum Press, New York.
2. Pier, G. B. (1985) *J. Infect. Dis.* 151:575–580.
3. Rivera, M., et al. (1982) *Am. Rev. Respir. Dis.* 126:833–836.
4. Todd, T. R. J., et al. (1989) *Am. Rev. Respir. Dis.* 140:1585–1589.
5. Irvin, R. T., et al. (1989) *Infect. Immun.* 57:3720–3726.
6. Lee, K. K., et al. (1989) *Mol. Microbiol.* 3:1493–1499.
7. Doig, P., et al. (1987) *Infect. Immun.* 55:1517–1522.
8. McEachran, D., et al. (1985) *Can. J. Microbiol.* 31:563–569.
9. Irvin, R. T., et al. (1990) *Microb. Ecol. Health Dis.* 3:39–47.
10. Bradley, D. E. (1972) *Genet. Res.* 19:39–51.
11. Folkhard, W. F., et al. (1981) *J. Mol. Biol.* 149:79–93.
12. Paranchych, W., et al. (1986) *Clin Invest Med* 9:113–118.
13. Paranchych, W., et al. (1990) "Expression, processing, and assembly of *Pseudomonas aeruginosa* N-methylphenylalanine pilin", in *Pseudomonas: Biotransformations, Pathogenesis and Evolving Biotechnology*, (Sliver, S., et al., eds.), pp 343–351, American Society for Microbiology, Washington, D.C.
14. Pasloske, B. L., et al. (1988) *J. Bacteriol.* 170:3738–3741.
15. Yu, L., et al. (1994) *Infect. Immun.* 62:5213–9.
16. Sheth, H. B., et al. (1994) *Mol. Microbiol.* 11:715–23.
17. Doig, P., et al. (1990) *Infect. Immun.* 58:124–130.
18. Lee, K. K., et al. (1989) *Infect. Immun.* 57:520–526.
19. Sheth, H. B., et al. (1995) *Biomed. Pept. Proteins and Nucleic Acids* 1:141–148.
20. Spangenberg, C., et al. (1995) *FEMS Microbiol Lett* 125:(2–3):265.
21. Koga, T., et al. (1993) *Infect Immunol* 61(4):1371.
22. Pafloski, B., et al. (1988) *Note in J. Bacteriol.* 170(8):3738.
23. Pafloski, B., et al. (1985) *FEBS Lett.* 183(2):408.
24. Sastry, P. A., et al. (1985) *J. Bacteriol.* 16(2):571.
25. Johnson, K., et al. (1986) *J. Biol Chem.* 261(33):15703.
26. Castric, P. A., et al. (1989) *Mol Gen Genet* 216(1):75.
27. Strom, M. S., et al. (1986) *J. Bacteriol.* 165(2):367.
28. Yi, T. M., et al. (1993) *J Mol Biol.* 232(4):1117.
29. Viswanadhan, V. N., et al. (1991) *Biochemistry* 30(46):11164.
30. King, R. D., et al. (1990) *J Mol Biol* 216(2):441.
31. Biou V., et al. (1988) *Protein Eng* 2(3):185.
32. Corrigan, A. J. (1982) *Comput Programs Biomed.* 15(3):163.
33. Tripet, B. L., et al. (1996) *Protein Eng* 9:1029.
34. Chao, H., et al. (1998) *J. Chrom A.* 715:307.
35. Zhou N. E., et al. (1993) *Biochemistry* 32:6190.
36. Gunasekaran, K., et al. (1998) *J Mol Biol* 6:917.
37. Paranchych, W., et al. (1988) *Advan Microbiol Phys* 29:53.
38. Paranchych, W., et al. (1979) *Can J. Microbiol* 25:1175.
39. Pasloske B. L., et al. (1988) *Mol Microbiol* 2:489.
40. Pasloske, B. L., et al. (1985) *FEBS Lett* 183:408.
41. Pasloske, B. L., et al. (1988) *J Bacteriol* 170:3738.

BACKGROUND OF THE INVENTION

*Pseudomonas aeruginosa* is a significant opportunistic pathogen that causes a variety of life-threatening infections in immunosuppressed or immunocompromised patients [1–4]. Individuals who are at risk of developing *P. aeruginosa* infections include cystic fibrosis patients, burn patients, severe neutropenic patients (e.g., cancer patients receiving chemotherapy) and intensive care unit patients receiving respiratory support. The cost of these infections is high, >60,000 lives per year in North America and about $5 billion/year in health care costs.

The first step in the Pseudomonas infection process appears to be the attachment to the host cell. This attachment is mediated by pili on the surface of the bacterium [2, 5, 6]. *P. aeruginosa* uses several adhesins to mediate attachment to mucosal surfaces, but analysis of the binding properties of the adhesins [1, 7, 8] and binding competition studies [9] indicate that the pilus is the dominant adhesin responsible for initiating infections [1].

*P. aeruginosa* pili have a structure resembling a hollow tube of about 5.2 nm in outer diameter, 1.2 nm in central channel diameter, and an average length of 2.5 $\mu$m [10–12]. The pilus of *P. aeruginosa* is composed of multiple copies of a 13–17 kDa monomeric protein subunit called pilin, which are capable of self-assembling into pili.

The C-terminal region of the pilin monomer contains the epithelial cell binding domain [5, 12], and is semiconserved in seven different strains of this bacterium [13, 14]. This semiconserved region has also been shown to bind to a minimal structural carbohydrate receptor sequence, $\beta$-GalNAc(1–4)$\beta$Gal, found in glycosphingolipids, specifically asialo-GM1 and asialo-GM2 [15, 16]. There is evidence that pili binding to a host cell is mediated multivalent binding of C-terminal binding domains in each pili to epithelial-cell receptors, with such binding serving to mobilize receptors on the cells. This, in turn, may be responsible to cytokine, e.g., IL-8 production by the host cells and consequent inflammatory response.

The C-terminal disulfide-bridged 17-residue region of the PAK pilin is known to be important in raising antibodies that block binding of both bacteria or their pili to epithelial cells [6, 17, 18]. Both monoclonal antisera generated from *P. aeruginosa* pili or polyclonal antisera generated from synthetic peptides representing the receptor binding domain of the pathogen have been shown to be efficacious in preventing infection [19].

The ability of antibodies produced against the C-terminal pilin-peptide domain to effectively inhibit Pseudomonas infection has been demonstrated (see, for example, U.S. Pat. No. 5,468,484), and the use of the pilin-peptide domain for use in vaccination against Pseudomonas infection has also been demonstrated, e.g., U.S. Pat. Nos. 5,445,818, 5,494, 672, and 5,612,036.

It would also be desirable to directly treat an existing Pseudomonas infection, or to treat an individual at risk of Pseudomonas infection prophylactically. Although intact pili have been proposed for this purpose, this method is limited by the fact that isolated, self-assembled pili have the ability to provoke a strong inflammatory response. Alternatively, the C-terminal pilin peptide has been proposed for this purpose, but this approach is limited by the relatively weak binding of the peptide to the host-cell receptor sites.

SUMMARY OF THE INVENTION

The invention includes, in one aspect, a composition for use in treating or preventing infection by *Pseudomonas aeruginosa*. The composition comprises a *P. aeruginosa* pilin protein having an N-terminal peptide region modified to prevent self assembly of the peptide. The peptide may be formulated in a pharmaceutically acceptable carrier, such as an aerosolizable liquid or particle vehicle, or an injectable solution.

In one general embodiment, the modified N-terminal peptide region lacks an N-terminal portion of native *P. aeruginosa*, preferably the first 15 up to the first 40 amino acids residues of native *P. aeruginosa*, more preferably the first 25 up to the first 30 amino acids.

In another general embodiment, the N-terminal region is modified, e.g., by amino acid substitutions, to prevent or inhibit alpha-helix formation in the N-terminal region, thereby preventing the pilin peptide from self-assembling.

In still another embodiment, the N-terminal region of the pilin peptide is replaced by a peptide moiety capable of forming a coiled-coil heterodimer or homodimer structure with an oppositely charged or identical alpha-helix forming peptide moiety, as represented by a so-called leucine zipper peptide. The modified pilin peptide can form dimeric structures which have higher binding affinity to host cells than the corresponding monomer, by virtue of divalent binding, but which are less inflammatory than intact pili, due to the reduced degree of mobilization of host-cell receptor sites, relative to that produced by binding of intact pili. Further, the dimeric construction allows pilin peptides from two different Pseudomonas strains to be assembled in dimeric form, or a combination of a single pilin peptide and another therapeutic agent, e.g., an antibacterial agent carried in cleavable form on a carrier peptide which forms the other monomer in the dimeric structure.

The modified pilin peptide may be further modified, in accordance with the invention, to reduce or eliminate immunogenicity in the target organism, e.g., humans.

In accordance with another aspect of the invention, the composition is used in treating or preventing *P. aeruginosa* infection in a subject a pharmaceutically effective amount of the modified *P. aeruginosa* pilin protein to the subject. The peptide is administered, for example, by formulating the peptide as a liquid or particulate aerosol, and delivering the aerosol to the subject's airway., or by intravenous administration.

These and other objects and features of the invention will become more fully apparent when the following detailed description of the invention is read in conjunction with the accompanying drawings.

BRIEF DESCRIPTION OF THE DRAWINGS

FIGS. 1A–1E give the nucleotide and corresponding amino acid sequence of an exemplary truncated pilin protein from K122 (1A), PAK (1B), PAO (1C), P1 (1D, and KB7 (1E), where the nucleotide and polypeptide sequences from K122, PAK, PAO, P1, and KB7 are identified by SEQ ID NOS: 1 and 2, SEQ ID NOS: 3 and 4, SEQ ID NOS: 5 and 6, SEQ ID NOS: 7 and 8, and SEQ ID NOS: 9 and 10, respectively;

FIGS. 2A and 2B show vector constructs designated pDLB42 and pDLB43 containing an N-terminal H coil-truncated PAK fusion peptide (2A), and an N-terminal E coil-truncated PAK fusion peptide (2B);

FIGS. 3A and 3B show the nucleotide and polypeptide sequences of an exemplary N-terminal H coil-truncated PAK fusion peptide (3A), and an exemplary N-terminal E coil-truncated PAK fusion peptide (3B) in the vector constructs in FIGS. 2A and 2B, respectively, where the nucleotide and polypeptides sequences are identified by SEQ ID NOS: 11 and 12, and SEQ ID NOS: 13 and 14, respectively;

FIGS. 4A and 4B show nucleotide and polypeptide sequences of an exemplary N-terminal H coil-truncated K122 fusion peptide (4A), and an exemplary N-terminal E coil-truncated K122 fusion peptide, respectively, where the nucleotide and polypeptides sequences are identified by SEQ ID NOS: 15 and 16, and SEQ ID NOS: 17 and 18, respectively;

FIGS. 5A and 5B show nucleotide and polypeptide sequences of an exemplary N-terminal H coil-truncated PAO peptide (5A), and an exemplary N-terminal E coil-truncated fusion PAO peptide, respectively, where the nucleotide and polypeptides sequences are identified by SEQ ID NOS: 19 and 20, and SEQ ID NOS: 21 and 22, respectively;

FIG. 6 illustrates steps in the purification of the K122 truncated pilin protein from FIG. 1A;

FIG. 7 is a plot of size exclusion chromatography of the truncated K122 pilin protein from FIG. 1A;

FIG. 8 is a plot of the competitive inhibition of biotinylated PAK pili binding to immobilized asialo-$GM_1$ by the truncated K122 pilin protein of FIG. 1A; and FIG. 9 illustrates the ability of a modified pilin protein formed in accordance with the invention to prolong survival in a mouse model of Pseudomonas infection;

DETAILED DESCRIPTION OF THE INVENTION

The first section describes exemplary modified Pseudomonas pilin peptides formed in accordance with the invention, and expression vectors for recombinant expression of the proteins. The second section provides procedures for constructing a model expression vector for a truncated PAK pilin protein, for isolating the protein, and a competitive binding assay for characterizing the modified protein's ability to bind to ASIALO-$GM_1$ glycosphingolipid. The method of treating or preventing Pseudomonas infection, in accordance with another aspect of the invention, and the effect of the treatment in a model animal system, is given in the third section.

I. Modified Pilin-Peptide Compositions

The invention takes advantage of the observation herein that the *P. aeruginosa* pilin protein can be modified to prevent self-assembly, i.e., oligomerization, by modifying the N terminus of the protein to prevent alpha helix formation, and the further observation herein that a monomeric or dimeric form of the pilin peptide is effective in treating or as a prophylactic for Pseudomonas infection, but without, or with a significantly reduced inflammatory response relative to intact pili. The N-terminal peptide modifications contemplated herein are of three general types:

(i) amino acid changes which alter the peptide's ability to form α-helical structures in the N-terminal portion of the protein, preferably in the first 2040 residues of the e.g., and (ii) deletions in the N-terminal portion of the peptide, e.g., a deletion of the first 15 to the first 40 N-terminal amino acids, preferably the first 25 to first 30 N-terminal amino acids; and (iii) replacement of the N-terminal portion with an alpha-helical coiled-coil homodimer or heterodimer sequence.

Amino acid modifications, e.g., substitutions, deletions, or additions in the N-terminal portion of the peptide effective to produce a non-self-assembling peptide can be determined from known physical interactions that determine the properties of proteins, and from the conformational properties of polypeptide chains. In particular, modifications that affect the ability of the N-terminal portion to disrupt α-helix formation in the first N-terminal 30 amino acid region of the protein will generally be pertinent. Introduction of Pro residues, in particular, in this segment of the protein will significantly disrupt a-helix formation, but other residues that tend to destabilize a-helices, e.g., groups of Gly, His or Asn, are also contemplated (see, for example, the discussion in Proteins, supra, pages, 182–186, and refs. 35 and 36). For example, a string of continuous Gly, His, or Asn residues, e.g., 3–5 residue string, will effectively prevent alpha helix formation, as will periodic Pro residues, e.g., every 5–7 residues.

The amino acid sequences of several Pseudomonas pilin peptides have been reported [e.g., 37–41]. Further, there is a large body of literature references that provide guidance as to the types and frequency of residues that will effectively prevent alpha-helix formation are available. From these references, one may construct specific amino acid substitutions, deletions, or additions that would be predicted to eliminate or reduce the tendency of alpha-helix formation in the first 1540 residues of a selected pilin peptide. Alternatively, a variety of computer algorithms designed to predict secondary structure may be employed to determine whether given amino acid substitutions in the N-terminal region of a selected Pseudomonas pilin peptide are likely to be effective in blocking alpha-helix formation [e.g., 25–32].

Alternatively, the N-terminal portion of the peptide may be deleted, to produce a pilin protein whose N-terminal region is lacking a critical i-helical forming portion. As noted above, the deletions in the N-terminal portion of the peptide, are preferably the first 15 to the first 40 N-terminal amino acids, preferably the first 25 to first 30 N-terminal amino acids. In one exemplary peptide described below, the pilin protein from strain K122 has N-terminal residues 1–28 deleted. This peptide is identified below as K-1224. The polynucleotide and corresponding polypeptide sequences of the modified protein are given in FIG. 1A, and are identified herein as SEQ ID NO: 1 (polynucleotide sequence) and SEQ ID NO: 2 (polypeptide sequence). The first five amino acid residues in the polypeptide sequence are not native to the K122 sequence, but are derived from an intrinsic coding sequence of the expression vector. The C-terminal residue of the polypeptide is the Pro residue immediately upstream of the two stop OCH codons; that is, the polypeptide sequence identified by SEQ ID NO:2 does not include the residues Ser—Ser-Lys-Leu-Gly downstream of the stop codons.

Similar polynucleotide and polypeptide sequence for truncated pilin peptides from PAK, PAO, P1, and KB7 Pseudomonas strains are given in FIGS. 1B–1E, respectively. The polynucleotide and polypeptide sequences for the truncated pilin peptide from strain PAK are identified as SEQ ID NOS:3 and 4, respectively (FIG. 1B; for the truncated pilin peptide from strain PAO, SEQ ID NOS:5 and 6, respectively (FIG. 1C); for the truncated pilin peptide from strain P1, SEQ ID NOS:7 and 8, respectively (FIG. 1D); and for the truncated pilin peptide from strain KB7, SEQ ID NOS:9 and 10, respectively (FIG. 1E).

The example below illustrates the recombinant production of the above truncated pilin protein, designated K1224, truncated to delete its N-terminal 28 amino acid residues. It will be recognized by one skilled in the art that a variety of procedures are available for producing *P. aeruginosa* pilin protein with a modified N-terminal region. For example, references 20–26 disclose various *P. aeruginosa* pilin protein genes. Reference 27 details methods for expressing pilin peptide in *E. coli*. These references are incorporated herein by reference.

It will be further appreciated that methods for modifying the N-terminal region of a pili protein gene, to achieve a desired modification in the protein, are well within the skill of persons skilled in the art. For example, site directed mutagenesis, including substitution, deletion, and addition mutations of the gene sequence can be carried out by well known methods, e.g., involving PCR primers. Similarly genes with various-length truncations can be prepared by standard means, as exemplified below.

FIGS. 1A–1E illustrate exemplary coding sequences for N-terminal region truncated pilin peptide. For compositions in which one or amino acids are substituted in the first 2040 residues, to prevent alpha-helix formation in the N-terminal region, the peptide has known pilin-peptide sequences (see references above relating to *P. aeruginosa* pilin sequence, e.g., references 5, 12, 13, and 14), but modified to contain amino acid substitutions or additions, e.g., Pro residues or Gly strings at suitable residue positions. For producing such modified proteins recombinantly, one can suitably modify the coding sequence for the corresponding pilin peptide, using standard techniques, such as site-directed mutagenesis, PCR amplification with suitable-sequence primers, or solid-phase synthesis.

In the third general embodiment of the composition of the invention, the N-terminal region of a pilin peptide, e.g., the first 1540 residues, is replaced by a peptide segment capable of forming a coiled-coil homodimer with an identical peptide segment, or a heterodimer with an oppositely charged peptide segment. Peptides with this coiled-coil dimer forming property have been disclosed, e.g., in PCT applications WO 97/12988 and WO 95/31480, which are incorporated herein by reference.

Exemplary coiled-coil peptides are referred to herein E coils, referring to negatively charged subunits whose charge is provided predominantly by glutamic acid residues, and K coils, referring to positively charged subunits whose charge is provided dominantly by lysine residues. The two coils, when mixed, form a stable 1:1 K:E dimer. One exemplary E coil sequence is given in FIGS. 3B–5B, where the E coil segment constitutes roughly residue numbers 13–53 of the given fusion peptide sequences. The sequence of a K-coil sequence suitable for dimerizing with this E coil is given in the two PCT applications above.

Alternatively, the coiled-coil segment may be a homodimer sequence, referred to herein as an H coil, capable of dimerizing with itself. Exemplary H coil sequences are given in FIGS. 3A–5A, where the H coil segment constitutes roughly residue numbers 13–53 of the given fusion-peptide sequences. When mixed, these two segment form a 1:1 H:H homodimer.

To produce a heterodimer modified pilin peptide, fusion proteins containing both E-coil and K-coil N-terminal segments are formed, then mixed to produce the desired dimer. The two different peptides forming the dimer may be modified pilin protein from the same strain, e.g., a PAK/PAK pilin dimer, or from two different strains, e.g., a PAK/K122 dimer. Alternatively, one of the two peptides may be a non-pilin related peptide, for example, a carrier protein that is itself a therapeutic peptide, e.g., peptide anti-bacterial agent, or a carrier protein derivatized with a therapeutic compound that can be cleaved from the carrier, e.g., by an esterase.

In the case of a homodimer, the two modified pilin proteins will in general be same, although homodimers with different strain pilin proteins or with a mixture of a pilin and non-pilin peptide, can be formed in a mixture of same-peptide and different-peptide dimers.

Figure 2B:
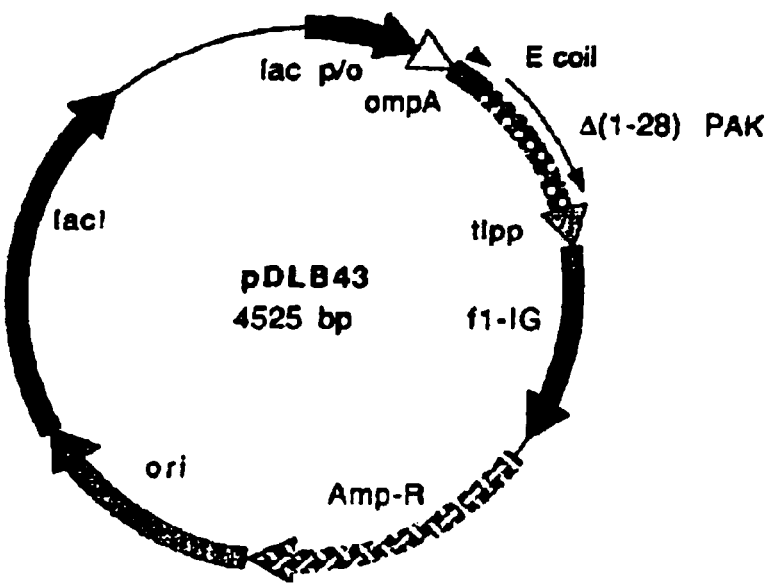

FIGS. 2A and 2B show the general construction of expression vectors for recombinant production in an $E.$ $coli$ host of modified pilin peptides (fusion peptides) with an N-terminal H coil-truncated pilin fusion peptide, in this case, the PAK peptide (2A), and an N-terminal E coil-truncated PAK pilin fusion peptide 2B). The vectors are constructed according to standard procedures, by inserting a suitable coding sequence into the pRLD vector cut with EcoR1 and HindIII [33, 34]. The polynucleotide sequence given in FIGS. 3–5 illustrate exemplary coding sequences for the fusion proteins that are inserted into the vectors.

FIGS. 3A and 3B show the nucleotide and polypeptide sequences of the N-terminal H coil-truncated PAK peptide (3A), and the N-terminal E coil-truncated PAK peptide (3B) in the vector constructs in FIGS. 2A and 2B, respectively. The nucleotide and polypeptides sequences are identified by SEQ ID NOS: 11 and 12 (H coil peptide), and SEQ ID NOS: 13 and 14 (E coil peptide), respectively. FIGS. 4A and 4B show nucleotide and polypeptide sequences for the H-coil and E-coil fusion proteins, respectively, where the sequences are identified by SEQ ID NOS: 15 and 16 (H-coil peptide), and SEQ ID NOS: 17 and 18 (E coil peptide), respectively. FIGS. 5A and 5B show nucleotide and polypeptide sequences of the N-terminal H coil-truncated PAO peptide (5A), and the N-terminal E coil-truncated PAO peptide (5B), respectively, where the nucleotide and polypeptides sequences are identified by SEQ ID NOS: 19 and 20 (H coil peptide), and SEQ ID NOS: 21 and 22 (E coil peptide, respectively).

The modified pilin peptide of the invention may be further modified to reduce or eliminate its immunogenicity in humans. This can be done, for example, following the approach disclosed in PCT application WO 98/52976, which is incorporated herein by reference. Briefly, the approach involves the steps of (a) determining at least part of the amino acid sequence of the protein, in this case, modified pilin peptide, (b) identifying in the amino acid sequence one or more potential epitopes for T-cells (T-cell epitopes) of the given species; and (c) modifying the amino acid sequence to eliminate at least one of the T-cell epitopes identified in step (b) thereby to eliminate or reduce the immunogenicity of the protein when exposed to the immune system of the given species.

II. Production and Characterization of Modified Pilin Proteins

A. Preparing the Coding Sequence and Construction of Expression Vector.

In one general method, modified pilin proteins are prepared by PCR amplification of known and available pilin coding sequences using primers that effect the desired deletion, modification or insertion of a coiled-coil moiety in the amplified coding sequences. The primers also provide suitable endonuclease cutting sequences at the amplified fragment termini for introduction into selected insertion sites of an expression vector. After amplification and endonuclease treatment, the coding sequence fragment is purified and placed in a suitable expression vector, e.g., an $E$ $coli$ expression vector, under the control od a suitable promoter, for host-cell expression. Example 1 below details construction of the coding sequence and an expression vector for the truncated PAK pilin peptide whose sequence in shown in FIG. 1A.

EXAMPLE 1

Polymerase Chain Reaction (PCR).

PCR was performed in Stratagene Robocycler 40, thermocycler, using the standard protocol. Each reaction mixture (a total of 10 ul) containing the reaction buffer 700 mM Tris HCL pH8.8, 200 mM $MgCl_2$, 200 uM each dNTP, template DNA (1 ug), 825 ng of each of the primers and 2.5 units of Taq polymerase were denatured for 10 min at 94° C., followed, by 30 amplification cycles (3 min denaturation, at 94° C., 2 min annealing at 58° C. and 2 min extension at 72° C.

DNA sequencing.

DNA from the cloned plasmid preparations were sequenced using the dideoxy nucleotide method of Sanger et al., in combination with appropriate oligonucleotides used as primers.

Truncated K1224 Pilin Protein Gene.

Truncated K122 (1-28) pilin gene was engineered by using polymerase chain reaction (PCR). First, previously cloned K122 DNA (22) containing pilin gene was subjected to PCR using the synthetic oligonucleotides primers (with restriction sites added for cloning purposes) flanking the beginning and end of the nucleotide residues corresponding to the amino acids 28 and 150. The resulting PCR product was purified by electrophoresis on an 8% polyacrylamide gel. Fragments of about 380 bp were isolated, and digested with Ecor1 and HindIII enzymes. The digests were purified by Phenol-extraction followed by ethanol precipitation. FIG. 1A shows the polynucleotide sequence, and corresponding amino acid sequence of the truncated pilin protein.

The purified digests were cloned into pRLD expression vector at Ecor1-HindiIII sites. The ligated plasmid DNA was transformed into an expression host BL21 strain. Plasmid DNAs were isolated from the Carbenicillin resistant recombinants by the cleared lysate method, and digested with restriction enzymes to check for the correct size inserts. Recombinant DNA containing the correct size inserts were sequenced from both the orientations as described above.

B. Expression of Modified Pilin Protein.

The recombinant protein is expressed in a suitable host under suitable expression conditions, according to well-known methods. For example, for bacterial synthesis, the protein may be obtained in the periplasmic space of the bacteria, or in secreted form in the host-cell culture medium. Example 2 below illustrates the expression of the above truncated PAK pilin protein in $E.$ $coli$.

EXAMPLE 2

$E.$ $coli$ cells (BL21) harboring the K122(1-28) plasmid containing K122 truncated pilin gene were grown at 37° C., with shaking in LB medium containing carbenicillin (100 $\mu$g/ml) to an A50 of 0.5–0.7. Production of recombinant protein was induced by the addition of isopropyl β-D-thiogalactopyranoside (IPTG) to a final concentration of 1 mM. The bacteria were then grown for an additional 8 hours at 37° C. The expressed periplasmic protein was extracted by osmotic shock as follows: The cells were harvested at 4,000 g for 10 min, at 4° C. and re-suspended in TES buffer (10 mM Tris-HCl, 5 mM EDTA, 20% sucrose, pH 8.0.) in a final volume of 80 ml per gram of wet weight. Cells were shaken gently at room temp (150 rpm) for 10 min. The suspension was then centrifuged and the resulting pellet was re-suspended in 5 mM ice-cold $MgSO_4$ (80 ml per gram of wet weight). The cell suspension was shaken gently for 30 min on ice, and subsequently centrifuged at 8,000 g for 15 min at 4° C. The supernatant continuing the periplasmic fraction was then further clarified by passing through a 0.45 $\mu$m filter and subsequently purified by the column chromatography as described.

C. Protein Purification.

Figure 6:
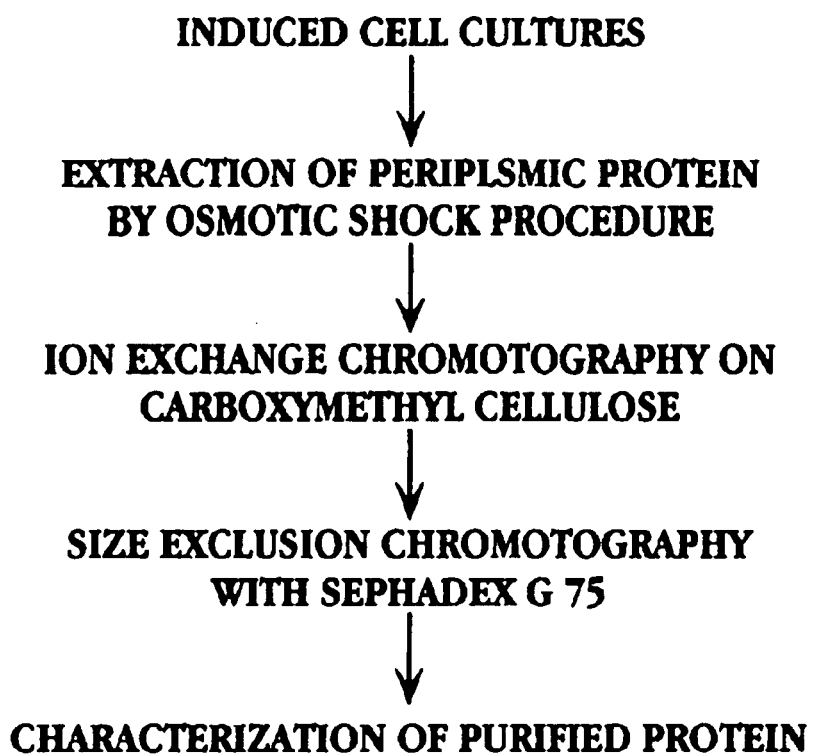

Methods that have been reported for purification of Pseudomonas pilin peptide are suitable, although some modification to accommodate the modified sequence may be required. In the case of a fusion pilin peptide having an N-terminal coiled-coil peptide moiety, the fusion protein can be isolated by affinity chromatography, using an immobilized coiled-coil peptide to capture the fusion protein. FIG. 6 illustrates a general scheme for purifying a modified pilin protein formed in accordance with the invention, as detailed in Example 3 below. It will be appreciated that the protein purification scheme is exemplary only.

EXAMPLE 3

Figure 7:
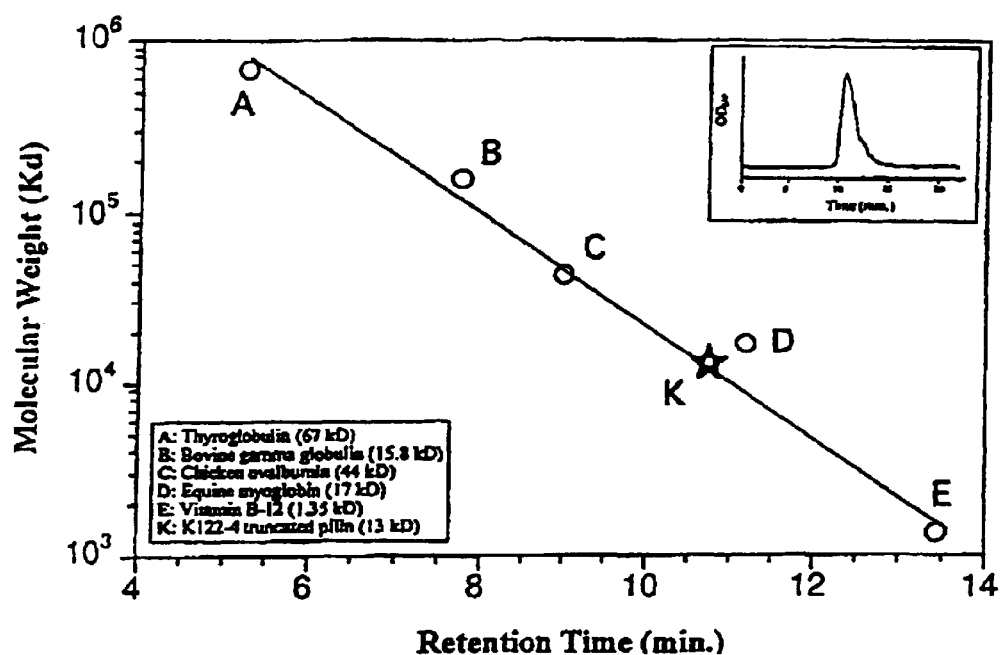

The periplasmic fractions from the transformed bacterial expression host cells were filtered through 0.45 $\mu$m filter and diluted with an equal volume of 20 mM sodium acetate pH 4.5 buffer and then adsorbed to a carboxymethyl-cellulose column (CM-52 of 30 cm×2 cm) which has been previously equilibrated with 10 mM sodium acetate pH 4.5 buffer (base buffer) and eluted with a linear gradient of 0–0.8M NaCl in 10 mM sodium acetate pH 4.5. Fractions (3 ml volume) were collected and the absorbance at A280 nm determined. Fractions containing pilin protein were pooled, freeze dried and dissolved in small amounts of distilled water, and further fractionated on a Sephadex G-75. As seen in FIG. 7, the molecular weight of the pilin protein (star on the plot) was about 13 KD, consistent with the 129 amino acid residue length of the protein (see FIG. 1A).

The isolated protein was fractionated by electrophoresis on sodium dodecyl sulfate-polyacrylamide gel electrophoresis (SDS-PAGE gels). Gels were subsequently stained with Coomassie brilliant blue R-250 or transferred to PVDF membranes. Membranes were incubated with K122 IgG antiserum. The secondary antibody used was anti-mouse IgG alkaline-phosphatase. Bound antibody was detected with BCIP substrate. The results (not shown) indicate a substantially pure protein.

D. Ability of Fusion Protein to Compete with Native Pili for Binding to Receptor Sites.

To confirm that the modified pilin peptide, including dimerized forms of the peptide, are capable of competing with pili for binding to receptor sites, the peptide may be tested in a competitive binding assay with native pili. The pili may be from same-strain or different-strain Pseudomonas organisms. Further to this point, the modified pilin can be tested against a number of different-strain pili, to test the cross-specificity the peptide is likely to have as a therapeutic agent. Example 4 below describes an exemplary binding assay of this type.

EXAMPLE 4

Figure 8:
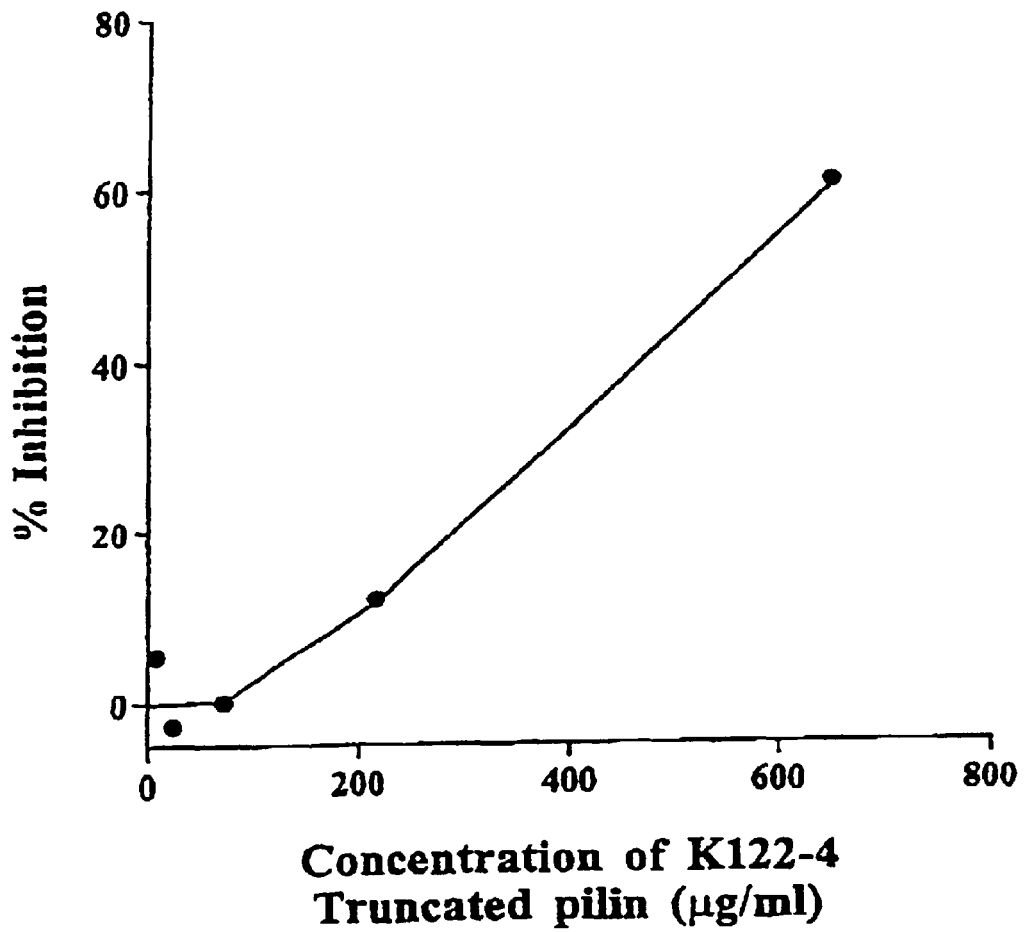

A polystyrene microtitre plate (Costar, Cambridge, Mass.) was coated with 50 $\mu$l/well of asialo-$GM_1$ (40 $\mu$g/ml) in methanol. The solvent was evaporated at room temperature inside a fumehood. Non-specific binding sites were blocked with 200 $\mu$l/well of 5% (w/v) BSA in PBS. After incubating at 37° C. for 1.5 hours, the wells were washed 3 times with 250 $\mu$l of PBS supplemented with 0.05% (w/v) BSA (Buffer A). Aliquots (50 $\mu$l) of biotinylated *P. aeruginosa* PAK pili (0.88 mg/ml, diluted 1:1000 in Buffer A) containing various concentrations of K1224 truncated pilin were added to each well. After a 2 hour incubation at 37° C. the wells were washed 5 times with 250 $\mu$l of Buffer A, then 50 $\mu$l/well of streptavidin-alkaline phosphatase conjugate (Gibco BRL) at 1:3000 dilution with Buffer A was added and incubated for 1 hour at room temperature. Following incubation, the plate was washed 5 times with 250 $\mu$l/well of Buffer A. Following washing 80 $\mu$l/well of p-nitrophenylphosphate substrate solution (1 mg/mil in 10% diethanolamine, pH 9.8) was then added. Readings at 405 nm were recorded and the results were expressed as percent inhibition. As seen in FIG. 8., the percent inhibition was dose dependent on the concentration of the truncated protein.

III. Treatment Method

The modified pilin peptide composition of the invention is useful in treating existing Pseudomonas infection, or as a prophylactic treatment for an individual at risk of Pseudomonas infection, e.g., cystic fibrosis patients, burn patients, and severe neutropenic patients (e.g., cancer patients receiving chemotherapy) and intensive care unit patients receiving respiratory support.

The peptide that is administered in the method may be modified in its N-terminal segment by deletion, substitution, or dimer-forming moieties, as detailed above. Further, the peptide may be modified, e.g., as detailed in WO98/52976 for reduced immunogenicity.

One preferred method of administration is by inhalation, typically in an aerosolized or microparticle form. Methods for preparing and administering peptides by aerosol are well known and suitable for this method. Typically, the amount of peptide administered is between about 0.5 to 25 mg/dose/patient, with the amount of peptide reaching the pulmonary airways depending on the efficiency of the aerosol and administration procedure. The peptide may be administered periodically, e.g., every 68 hours, over a period until a satisfactory therapeutic end point is reached.

Alternatively, the peptide may be administered by transmucosal route, e.g., intranasally, or through intravenous (IV), intraperitoneal (IP), intramuscular (IM), or subcutaneous (SubQ) injection. Typically, doses in an amount of 1 mg to 50 mg, administered once a day or over a more frequent dosing schedule, are suitable, although higher doses may be required for IP, IM, or SubQ administration, do to the relatively slow peptide release and uptake at sites if infection. Transdermal administration may also be effective assuming that the peptide can be taken up efficiently by this route. Example 5 below demonstrates therapeutic efficacy when the peptide is administered intraperitoneally.

For prophylactic administration, the peptide may be administered in a single dose, or multiple doses, e.g., every 8 hours, for a period preceding elevated risk of infection, at peptide doses similar to those given above.

In the treatment method, the peptide may be administered in conjunction with anti-bacterial agents, typically non-peptide agents, conventionally used to treat Pseudomonas infection.

EXAMPLE 5

Figure 9:
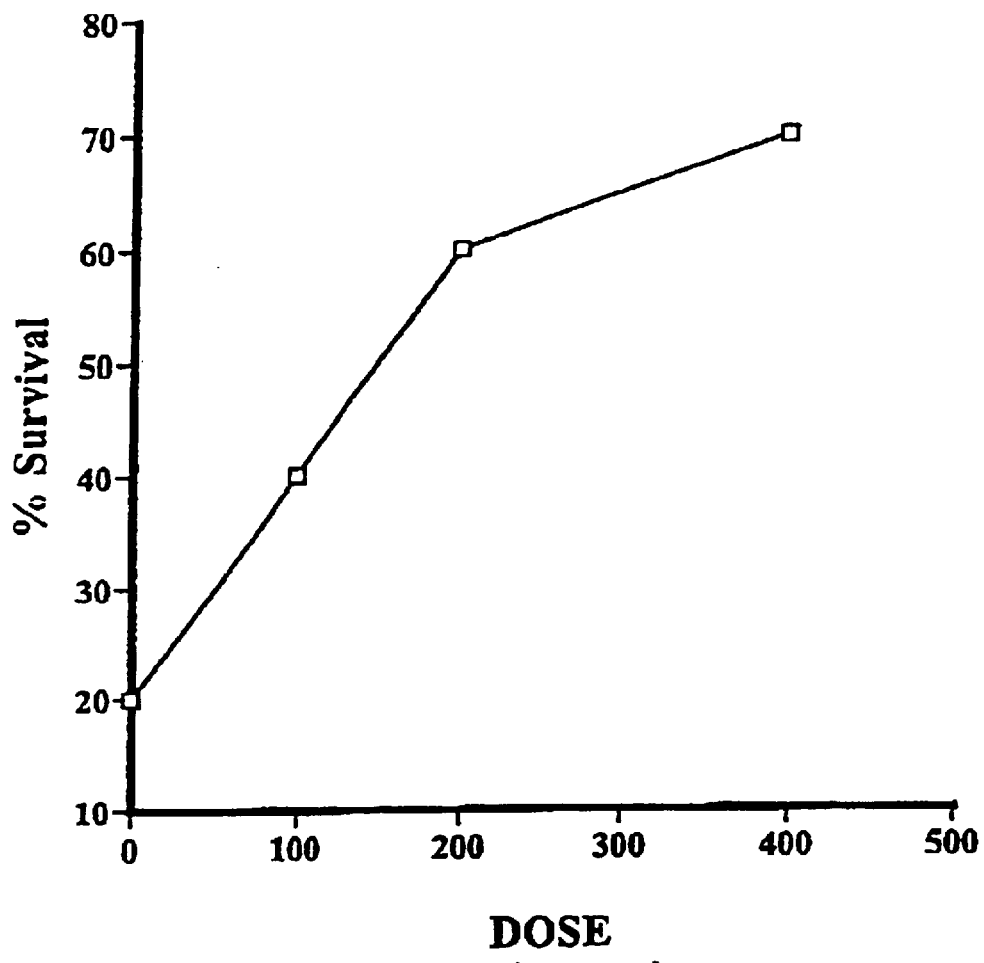

A.BY/SnJ mice were used as they are less resistant to *P. aeruginosa* infection than other mouse strains. Weight:

18–20 grams; age: 10 weeks. K1224-4 truncated pilin (FIG. 1A) was administered intraperitoneally to A.BY/SnJ mice 15 minutes prior to the mice being challenged intraperitoneally with PAK wildtype at 3LD$_{50}$. Mice were monitored on a hourly basis between 16 and 48 hours. As seen in FIG. 9, percent survival was dose dependent within the range of pilin protein amounts tested.

From the foregoing, it can be seen that (i) an N-terminal modified pilin protein unable to oligomerize (self-assemble) is readily expressed as a secreted processed protein in a recombinant expression system; (ii) the modified protein retains a functional epithelial cell receptor binding domain that mediates binding to GalNAcGal containing glycoconjugates; (iii) the modified protein is monomeric at protein concentrations of <600 µg/ml; and (iv), pre-administration of the modified protein confers a dose-dependent protection from challenge with a heterologous *P. aeruginosa* strain in mammals.

Although the invention has been described with respect to specific embodiments, it will be appreciated that the a variety of different pilin peptide N-terminal modifications, and a variety of different *P. aeruginosa* strains may be employed without departing from the invention.

Sequence Listing

SEQ ID NO: 1: polynucleotide sequence of modified K122 pilin peptide;
SEQ ID NO: 2 polypeptide sequence of modified K122 pilin peptide;
SEQ ID NO: 3: polynucleotide sequence of modified PAK pilin peptide;
SEQ ID NO: 4 polypeptide sequence of modified PAK pilin peptide;
SEQ ID NO: 5: polynucleotide sequence of modified PAO pilin peptide;
SEQ ID NO: 6: polypeptide sequence of modified PAO pilin peptide;
SEQ ID NO: 7: polynucleotide sequence of modified P1 pilin peptide;
SEQ ID NO: 8: polypeptide sequence of modified P1 pilin peptide;
SEQ ID NO: 9: polynucleotide sequence of modified KB7 pilin peptide;
SEQ ID NO: 10: polypeptide sequence of modified KB7 pilin peptide;
SEQ ID NO: 11: polynucleotide sequence of H-coil/truncated PAK pilin peptide;
SEQ ID NO: 12: polypeptide sequence of H-coil/truncated PAK pilin peptide;
SEQ ID NO: 13: polynucleotide sequence of E-coil/truncated PAK pilin peptide;
SEQ ID NO: 14: polypeptide sequence of E-coil/truncated PAK pilin peptide;
SEQ ID NO: 15: polynucleotide sequence of H-coil/truncated K122 pilin peptide;
SEQ ID NO: 16: polypeptide sequence of H-coil/truncated K122 pilin peptide;
SEQ ID NO: 17: polynucleotide sequence of E-coil/truncated K122 pilin peptide;
SEQ ID NO: 18: polypeptide sequence of E-coil/truncated K122 pilin peptide;
SEQ ID NO: 19: polynucleotide sequence of H-coil/truncated PAO pilin peptide;
SEQ ID NO: 20: polypeptide sequence of H-coil/truncated PAO pilin peptide;
SEQ ID NO: 21: polynucleotide sequence of E-coil/truncated PAO pilin peptide;
SEQ ID NO: 22: polypeptide sequence of E-coil/truncated PAO pilin peptide;

It is claimed:

1. A method of treating or preventing infection by *Pseudomonas aeruginosa* comprising administering a pharmaceutically acceptable amount of an isolated pilin peptide having the amino acid sequence set forth in SEQ ID Nos. 4, 6, 8, or 10.

* * * * *

SEQUENCE LISTING

```
<160> NUMBER OF SEQ ID NOS: 22

<210> SEQ ID NO 1
<211> LENGTH: 387
<212> TYPE: DNA
<213> ORGANISM: Pseudomonas aeruginosa
<220> FEATURE:
<221> NAME/KEY: CDS
<222> LOCATION: (0)...(0)

<400> SEQUENCE: 1
gcgctcgagg gtaccgaatt cgcacgcgct cagcttagcg aacgcatgac cctggccagt      60
ggtctcaaga cgaaagtgag cgatatcttc tctcaggatg ggtcctgccc ggctaatact     120
gctgccacgg caggcatcga gaaagatacc gacatcaacg gcaagtatgt tgccaaggta     180
acaactggtg gcaccgcagc tgcgtctggt ggttgcacta tcgttgctac tatgaaagcc     240
tctgatgtgg ctactcctct gaggggggaaa actctgactt tgactctagg aaatgctgac     300
aagggttctt acacttgggc ctgtacttcc aacgcagata caagtacct gccaaaaacc      360 tgccagactg ctaccactac cactccg                                         387

<210> SEQ ID NO 2
<211> LENGTH: 129
<212> TYPE: PRT
```

<213> ORGANISM: Pseudomonas aeruginosa

<400> SEQUENCE: 2

```
Ala Leu Glu Gly Thr Glu Phe Ala Arg Ala Gln Leu Ser Glu Arg Met
 1               5                  10                  15
Thr Leu Ala Ser Gly Leu Lys Thr Lys Val Ser Asp Ile Phe Ser Gln
            20                  25                  30
Asp Gly Ser Cys Pro Ala Asn Thr Ala Thr Ala Gly Ile Glu Lys
        35                  40                  45
Asp Thr Asp Ile Asn Gly Lys Tyr Val Ala Lys Val Thr Gly Gly
    50                  55                  60
Thr Ala Ala Ser Gly Gly Cys Thr Ile Val Ala Thr Met Lys Ala
65                  70                  75                  80
Ser Asp Val Ala Thr Pro Leu Arg Gly Lys Thr Leu Thr Leu Thr Leu
                85                  90                  95
Gly Asn Ala Asp Lys Gly Ser Tyr Thr Trp Ala Cys Thr Ser Asn Ala
               100                 105                 110
Asp Asn Lys Tyr Leu Pro Lys Thr Cys Gln Thr Ala Thr Thr Thr
           115                 120                 125
Pro
```

<210> SEQ ID NO 3
<211> LENGTH: 369
<212> TYPE: DNA
<213> ORGANISM: Pseudomonas aeruginosa

<400> SEQUENCE: 3

```
gcgctcgagg gtaccgaatt cgctcgttcg gaaggcgcat ctgctcttgc ttcggtcaat      60
ccgttgaaga ctaccgttga agaggcgctt tctcgtggtt ggagcgtgaa gagcggtaca     120
ggtacagagg acgctactaa gaaagaggtt cctctggggg tggcggcaga tgctaacaaa     180
ctgggtacta tcgcactcaa acccgatcct gctgatggta ctgcagatat cactttgact     240
ttcactatgg gcggtgcagg accgaagaat aaagggaaaa ttattaccct gactcgtact     300
gcagctgatg gtctctggaa gtgcaccagt gatcaggatg agcagtttat tccgaaaggt     360
tgctctagg                                                             369
```

<210> SEQ ID NO 4
<211> LENGTH: 123
<212> TYPE: PRT
<213> ORGANISM: Pseudomonas aeruginosa

<400> SEQUENCE: 4

```
Ala Leu Glu Gly Thr Glu Phe Ala Arg Ser Glu Gly Ala Ser Ala Leu
 1               5                  10                  15
Ala Ser Val Asn Pro Leu Lys Thr Thr Val Glu Glu Ala Leu Ser Arg
            20                  25                  30
Gly Trp Ser Val Lys Ser Gly Thr Gly Thr Glu Asp Ala Thr Lys Lys
        35                  40                  45
Glu Val Pro Leu Gly Val Ala Ala Asp Ala Asn Lys Leu Gly Thr Ile
    50                  55                  60
Ala Leu Lys Pro Asp Pro Ala Asp Gly Thr Ala Asp Ile Thr Leu Thr
65                  70                  75                  80
Phe Thr Met Gly Gly Ala Gly Pro Lys Asn Lys Gly Lys Ile Ile Thr
                85                  90                  95
Leu Thr Arg Thr Ala Ala Asp Gly Leu Trp Lys Cys Thr Ser Asp Gln
```

```
                     100             105             110
Asp Glu Gln Phe Ile Pro Lys Gly Cys Ser Arg
        115             120

<210> SEQ ID NO 5
<211> LENGTH: 366
<212> TYPE: DNA
<213> ORGANISM: Pseudomonas aeruginosa
<220> FEATURE:
<221> NAME/KEY: CDS
<222> LOCATION: (0)...(0)

<400> SEQUENCE: 5
gcgctcgagg gtaccgaatt cgcgcgttcg gaaggtgctt cggcgctggc gacgatcaac      60
ccgctgaaga ccactgttga agagtcgctg tcgcgtggaa ttgctggtag caaaattaaa     120
attggtacta ctgcttctac tgcgaccgaa acatatgccg gcgtcgagcc ggatgccaac     180
aagttgggtg taattgctgt agcaatcgaa gatagtggtg cgggtgatat tacctttacc     240
ttccagactg gtacctctag tcccaagaat gctactaaag ttatcactct gaaccgtact     300
gcggatgggg tctgggcttg taaatctacc caggatccga tgttcactcc gaaaggttct     360
gataac                                                                366

<210> SEQ ID NO 6
<211> LENGTH: 122
<212> TYPE: PRT
<213> ORGANISM: Pseudomonas aeruginosa

<400> SEQUENCE: 6

Ala Leu Glu Gly Thr Glu Phe Ala Arg Ser Glu Gly Ala Ser Ala Leu
 1               5                  10                  15

Ala Thr Ile Asn Pro Leu Lys Thr Thr Val Glu Glu Ser Leu Ser Arg
            20                  25                  30

Gly Ile Ala Gly Ser Lys Ile Lys Ile Gly Thr Thr Ala Ser Thr Ala
        35                  40                  45

Thr Glu Thr Tyr Ala Gly Val Glu Pro Asp Ala Asn Lys Leu Gly Val
    50                  55                  60

Ile Ala Val Ala Ile Glu Asp Ser Gly Ala Gly Asp Ile Thr Phe Thr
65                  70                  75                  80

Phe Gln Thr Gly Thr Ser Ser Pro Lys Asn Ala Thr Lys Val Ile Thr
                85                  90                  95

Leu Asn Arg Thr Ala Asp Gly Val Trp Ala Cys Lys Ser Thr Gln Asp
            100                 105                 110

Pro Met Phe Thr Pro Lys Gly Ser Asp Asn
        115                 120

<210> SEQ ID NO 7
<211> LENGTH: 381
<212> TYPE: DNA
<213> ORGANISM: Pseudomonas aeruginosa
<220> FEATURE:
<221> NAME/KEY: CDS
<222> LOCATION: (0)...(0)

<400> SEQUENCE: 7
gcgctcgagg gtaccgaatt cgcccgtacc caggtgaccc gtgccgtgag tgaagtcagc      60
gcgctgaaga ccgctgcgga gtcggcgatt ctggaaggga aggagattgt ttccagcgcg     120
actcctaaag atacccagta tgacattggc ttcaccgagt ctactttgct agatggttct     180
```

```
ggtaagagtc agatccaggt aacggacaat aaagatggca ccgttgagtt ggtcgctacc    240
ttgggtaaat cttctggttc cgccatcaaa ggggctgtaa tcactgtttc gcgtaaaaat    300
gacggagtct ggaactgcaa aatcaccaaa actcctacag cttggaagcc caactacgct    360
ccggctaatt gcccgaattc c                                              381
```

<210> SEQ ID NO 8
<211> LENGTH: 127
<212> TYPE: PRT
<213> ORGANISM: Pseudomonas aeruginosa

<400> SEQUENCE: 8

```
Ala Leu Glu Gly Thr Glu Phe Ala Arg Thr Gln Val Thr Arg Ala Val
 1               5                  10                  15

Ser Glu Val Ser Ala Leu Lys Thr Ala Ala Glu Ser Ala Ile Leu Glu
                20                  25                  30

Gly Lys Glu Ile Val Ser Ser Ala Thr Pro Lys Asp Thr Gln Tyr Asp
            35                  40                  45

Ile Gly Phe Thr Glu Ser Thr Leu Leu Asp Gly Ser Gly Lys Ser Gln
        50                  55                  60

Ile Gln Val Thr Asp Asn Lys Asp Gly Thr Val Glu Leu Val Ala Thr
65                  70                  75                  80

Leu Gly Lys Ser Ser Gly Ser Ala Ile Lys Gly Ala Val Ile Thr Val
                85                  90                  95

Ser Arg Lys Asn Asp Gly Val Trp Asn Cys Lys Ile Thr Lys Thr Pro
            100                 105                 110

Thr Ala Trp Lys Pro Asn Tyr Ala Pro Ala Asn Cys Pro Asn Ser
        115                 120                 125
```

<210> SEQ ID NO 9
<211> LENGTH: 381
<212> TYPE: DNA
<213> ORGANISM: Pseudomonas aeruginosa
<220> FEATURE:
<221> NAME/KEY: CDS
<222> LOCATION: (0)...(0)

<400> SEQUENCE: 9

```
gcgctcgagg gtaccgaatt ctctcgctct caggtctcca gggttatggc ggaggctggc     60
tccttgaaga ctgcagttga ggcctgcctc caggatggtc gtactgctgt gggtactgct    120
gctggtcaat gcgatccggg tgcgacgggt tccagtttgt tgactggtgc ttctcagact    180
tctcaaaccc tgccaaccaa taccggtgtt ccgcaggttc tggatcctct gactactcaa    240
accactatca ttgcgacttt tggtaacggc gcatccgcag ctatttctgg ccagactctg    300
acctggactc gtgatgttaa tggtggctgg agctgtgcta ctaccgtaga tgctaaattc    360
cgtcctaatg gctgtactga c                                              381
```

<210> SEQ ID NO 10
<211> LENGTH: 127
<212> TYPE: PRT
<213> ORGANISM: Pseudomonas aeruginosa

<400> SEQUENCE: 10

```
Ala Leu Glu Gly Thr Glu Phe Ser Arg Ser Gln Val Ser Arg Val Met
 1               5                  10                  15

Ala Glu Ala Gly Ser Leu Lys Thr Ala Val Glu Ala Cys Leu Gln Asp
                20                  25                  30
```

```
Gly Arg Thr Ala Val Gly Thr Ala Ala Gly Gln Cys Asp Pro Gly Ala
        35                  40                  45

Thr Gly Ser Ser Leu Leu Thr Gly Ala Ser Gln Thr Ser Gln Thr Leu
    50                  55                  60

Pro Thr Asn Thr Gly Val Pro Gln Val Leu Asp Pro Leu Thr Thr Gln
65                  70                  75                  80

Thr Thr Ile Ile Ala Thr Phe Gly Asn Gly Ala Ser Ala Ala Ile Ser
                85                  90                  95

Gly Gln Thr Leu Thr Trp Thr Arg Asp Val Asn Gly Gly Trp Ser Cys
            100                 105                 110

Ala Thr Val Asp Ala Lys Phe Arg Pro Asn Gly Cys Thr Asp
            115                 120                 125

<210> SEQ ID NO 11
<211> LENGTH: 507
<212> TYPE: DNA
<213> ORGANISM: Pseudomonas aeruginosa
<220> FEATURE:
<221> NAME/KEY: CDS
<222> LOCATION: (0)...(0)

<400> SEQUENCE: 11
gcgctcgagc accatcatca ccatggtggt ggtggcgaga ttgaggccct caaggctgaa      60
atcgaagccc taaaggccga gatagaagca cttaaggcag agatcgaggc gctaaaagcg     120
gaaatagagg ctctgaaggc aggcggtgga ggagaattcg ctcgttcgga aggcgcatct     180
gctcttgctt cggtcaatcc gttgaagact accgttgaag aggcgctttc tcgtggtttgg    240 agcgtgaaga gcggtacagg tacagaggac gctactaaga aagaggttcc tctgggggtg     300
gcggcagatg ctaacaaact gggtactatc gcactcaaac ccgatcctgc tgatggtact     360
gcagatatca ctttgacttt cactatgggc ggtgcaggac cgaagaataa agggaaaatt     420
attaccctga ctcgtactgc agctgatggt ctctggaagt gcaccagtga tcaggatgag     480
cagtttattc cgaaaggttg ctctagg                                          507

<210> SEQ ID NO 12
<211> LENGTH: 169
<212> TYPE: PRT
<213> ORGANISM: Pseudomonas aeruginosa

<400> SEQUENCE: 12

Ala Leu Glu His His His His Gly Gly Gly Gly Glu Ile Glu Ala
1               5                   10                  15

Leu Lys Ala Glu Ile Glu Ala Leu Lys Ala Glu Ile Glu Ala Leu Lys
            20                  25                  30

Ala Glu Ile Glu Ala Leu Lys Ala Glu Ile Glu Ala Leu Lys Ala Gly
        35                  40                  45

Gly Gly Gly Glu Phe Ala Arg Ser Glu Gly Ala Ser Ala Leu Ala Ser
    50                  55                  60

Val Asn Pro Leu Lys Thr Thr Val Glu Glu Ala Leu Ser Arg Gly Trp
65                  70                  75                  80

Ser Val Lys Ser Gly Thr Gly Thr Glu Asp Ala Thr Lys Lys Glu Val
                85                  90                  95

Pro Leu Gly Val Ala Ala Asp Ala Asn Lys Leu Gly Thr Ile Ala Leu
            100                 105                 110

Lys Pro Asp Pro Ala Asp Gly Thr Ala Asp Ile Thr Leu Thr Phe Thr
        115                 120                 125
```

```
Met Gly Gly Ala Gly Pro Lys Asn Lys Gly Lys Ile Ile Thr Leu Thr
    130                 135                 140

Arg Thr Ala Ala Asp Gly Leu Trp Lys Cys Thr Ser Asp Gln Asp Glu
145                 150                 155                 160

Gln Phe Ile Pro Lys Gly Cys Ser Arg
                165
```

```
<210> SEQ ID NO 13
<211> LENGTH: 507
<212> TYPE: DNA
<213> ORGANISM: Pseudomonas aeruginosa
<220> FEATURE:
<221> NAME/KEY: CDS
<222> LOCATION: (0)...(0)

<400> SEQUENCE: 13
```

| | | | | | |
|---|---|---|---|---|---|
| gcgctcgagc | accatcatca | ccatggtggt | ggtggcgagg | tatccgcttt | agagaaagaa | 60 |
| gtttctgctc | tcgaaaaaga | ggtcagtgct | ctggaaaaag | aggtgtcagc | cttggaaaag | 120 |
| gaagtatcag | cacttgagaa | gggcggtgga | ggagaattcg | ctcgttcgga | aggcgcatct | 180 |
| gctcttgctt | cggtcaatcc | gttgaagact | accgttgaag | aggcgctttc | tcgtggttgg | 240 |
| agcgtgaaga | gcggtacagg | tacagaggac | gctactaaga | aagaggttcc | tctggggtg | 300 |
| gcggcagatg | ctaacaaact | gggtactatc | gcactcaaac | ccgatcctgc | tgatggtact | 360 |
| gcagatatca | ctttgacttt | cactatgggc | ggtgcaggac | cgaagaataa | agggaaaatt | 420 |
| attaccctga | ctcgtactgc | agctgatggt | ctctggaagt | gcaccagtga | tcaggatgag | 480 |
| cagtttattc | cgaaaggttg | ctctagg | | | | 507 |

```
<210> SEQ ID NO 14
<211> LENGTH: 169
<212> TYPE: PRT
<213> ORGANISM: Pseudomonas aeruginosa

<400> SEQUENCE: 14
```

```
Ala Leu Glu His His His His His Gly Gly Gly Gly Glu Val Ser Ala
  1               5                  10                  15

Leu Glu Lys Glu Val Ser Ala Leu Glu Lys Glu Val Ser Ala Leu Glu
                 20                  25                  30

Lys Glu Val Ser Ala Leu Glu Lys Glu Val Ser Ala Leu Glu Lys Gly
             35                  40                  45

Gly Gly Gly Glu Phe Ala Arg Ser Glu Gly Ala Ser Ala Leu Ala Ser
         50                  55                  60

Val Asn Pro Leu Lys Thr Thr Val Glu Glu Ala Leu Ser Arg Gly Trp
 65                  70                  75                  80

Ser Val Lys Ser Gly Thr Gly Thr Glu Asp Ala Thr Lys Lys Glu Val
                 85                  90                  95

Pro Leu Gly Val Ala Ala Asp Ala Asn Lys Leu Gly Thr Ile Ala Leu
            100                 105                 110

Lys Pro Asp Pro Ala Asp Gly Thr Ala Asp Ile Thr Leu Thr Phe Thr
        115                 120                 125

Met Gly Gly Ala Gly Pro Lys Asn Lys Gly Lys Ile Ile Thr Leu Thr
    130                 135                 140

Arg Thr Ala Ala Asp Gly Leu Trp Lys Cys Thr Ser Asp Gln Asp Glu
145                 150                 155                 160

Gln Phe Ile Pro Lys Gly Cys Ser Arg
                165
```

<210> SEQ ID NO 15
<211> LENGTH: 525
<212> TYPE: DNA
<213> ORGANISM: Pseudomonas aeruginosa
<220> FEATURE:
<221> NAME/KEY: CDS
<222> LOCATION: (0)...(0)

<400> SEQUENCE: 15

```
gcgctcgagc accatcatca ccatggtggt ggtggcgaga ttgaggccct caaggctgaa      60
atcgaagccc taaaggccga gatagaagca cttaaggcag agatcgaggc gctaaaagcg     120
gaaatagagg ctctgaaggc aggcggtgga ggagaattcg cacgcgctca gcttagcgaa     180
cgcatgaccc tggccagtgg tctcaagacg aaagtgagcg atatcttctc tcaggatggg     240
tcctgcccgg ctaatactgc tgccacggca ggcatcgaga agataccga catcaacggc      300
aagtatgttg ccaaggtaac aactggtggc accgcagctg cgtctggtgg ttgcactatc     360
gttgctacta tgaaagcctc tgatgtggct actcctctga ggggaaaac tctgactttg      420
actctaggaa atgctgacaa gggttcttac acttgggcct gtacttccaa cgcagataac     480
aagtacctgc caaaaacctg ccagactgct accactacca ctccg                     525
```

<210> SEQ ID NO 16
<211> LENGTH: 175
<212> TYPE: PRT
<213> ORGANISM: Pseudomonas aeruginosa

<400> SEQUENCE: 16

```
Ala Leu Glu His His His His His Gly Gly Gly Gly Glu Ile Glu Ala
 1               5                  10                  15

Leu Lys Ala Glu Ile Glu Ala Leu Lys Ala Glu Ile Glu Ala Leu Lys
                20                  25                  30

Ala Glu Ile Glu Ala Leu Lys Ala Glu Ile Glu Ala Leu Lys Ala Gly
            35                  40                  45

Gly Gly Gly Glu Phe Ala Arg Ala Gln Leu Ser Glu Arg Met Thr Leu
        50                  55                  60

Ala Ser Gly Leu Lys Thr Lys Val Ser Asp Ile Phe Ser Gln Asp Gly
65                  70                  75                  80

Ser Cys Pro Ala Asn Thr Ala Ala Thr Ala Gly Ile Glu Lys Asp Thr
                85                  90                  95

Asp Ile Asn Gly Lys Tyr Val Ala Lys Val Thr Thr Gly Gly Thr Ala
            100                 105                 110

Ala Ala Ser Gly Gly Cys Thr Ile Val Ala Thr Met Lys Ala Ser Asp
        115                 120                 125

Val Ala Thr Pro Leu Arg Gly Lys Thr Leu Thr Leu Thr Leu Gly Asn
    130                 135                 140

Ala Asp Lys Gly Ser Tyr Thr Trp Ala Cys Thr Ser Asn Ala Asp Asn
145                 150                 155                 160

Lys Tyr Leu Pro Lys Thr Cys Gln Thr Ala Thr Thr Thr Pro
                165                 170                 175
```

<210> SEQ ID NO 17
<211> LENGTH: 525
<212> TYPE: DNA
<213> ORGANISM: Pseudomonas aeruginosa
<220> FEATURE:
<221> NAME/KEY: CDS
<222> LOCATION: (0)...(0)

-continued

```
<400> SEQUENCE: 17
gcgctcgagc accatcatca ccatggtggt ggtggcgagg tatccgcttt agagaaagaa      60
gtttctgctc tcgaaaaaga ggtcagtgct ctggaaaaag aggtgtcagc cttggaaaag     120
gaagtatcag cacttgagaa gggcggtgga ggagaattcg cacgcgctca gcttagcgaa     180
cgcatgaccc tggccagtgg tctcaagacg aaagtgagcg atatcttctc tcaggatggg     240
tcctgcccgg ctaatactgc tgccacggca ggcatcgaga agataccga catcaacggc      300 aagtatgttg ccaaggtaac aactggtggc accgcagctg cgtctggtgg ttgcactatc     360
gttgctacta tgaaagcctc tgatgtggct actcctctga gggggaaaac tctgactttg     420
actctaggaa atgctgacaa gggttcttac acttgggcct gtacttccaa cgcagataac     480
aagtacctgc aaaaacctg ccagactgct accactacca ctccg                      525
```

```
<210> SEQ ID NO 18
<211> LENGTH: 175
<212> TYPE: PRT
<213> ORGANISM: Pseudomonas aeruginosa

<400> SEQUENCE: 18

Ala Leu Glu His His His His His Gly Gly Gly Gly Glu Val Ser Ala
 1               5                  10                  15

Leu Glu Lys Glu Val Ser Ala Leu Glu Lys Glu Val Ser Ala Leu Glu
            20                  25                  30

Lys Glu Val Ser Ala Leu Glu Lys Glu Val Ser Ala Leu Glu Lys Gly
        35                  40                  45

Gly Gly Gly Glu Phe Ala Arg Ala Gln Leu Ser Glu Arg Met Thr Leu
    50                  55                  60

Ala Ser Gly Leu Lys Thr Lys Val Ser Asp Ile Phe Ser Gln Asp Gly
65                  70                  75                  80

Ser Cys Pro Ala Asn Thr Ala Ala Thr Ala Gly Ile Glu Lys Asp Thr
                85                  90                  95

Asp Ile Asn Gly Lys Tyr Val Ala Lys Val Thr Thr Gly Gly Thr Ala
            100                 105                 110

Ala Ala Ser Gly Gly Cys Thr Ile Val Ala Thr Met Lys Ala Ser Asp
        115                 120                 125

Val Ala Thr Pro Leu Arg Gly Lys Thr Leu Thr Leu Thr Leu Gly Asn
    130                 135                 140

Ala Asp Lys Gly Ser Tyr Thr Trp Ala Cys Thr Ser Asn Ala Asp Asn
145                 150                 155                 160

Lys Tyr Leu Pro Lys Thr Cys Gln Thr Ala Thr Thr Thr Pro
                165                 170                 175
```

```
<210> SEQ ID NO 19
<211> LENGTH: 504
<212> TYPE: DNA
<213> ORGANISM: Pseudomonas aeruginosa
<220> FEATURE:
<221> NAME/KEY: CDS
<222> LOCATION: (0)...(0)

<400> SEQUENCE: 19
gcgctcgagc accatcatca ccatggtggt ggtggcgaga ttgaggccct caaggctgaa     60
atcgaagccc taaggccga gatagaagca cttaaggcag agatcgaggc gctaaaagcg     120
gaaatagagg ctctgaaggc aggcggtgga ggagaattcg cgcgttcgga aggtgcttcg     180
gcgctggcga cgatcaaccc gctgaagacc actgttgaag agtcgctgtc gcgtggaatt     240
```

```
gctggtagca aaattaaaat tggtactact gcttctactg cgaccgaaac atatgccggc      300
gtcgagccgg atgccaacaa gttgggtgta attgctgtag caatcgaaga tagtggtgcg      360
ggtgatatta cctttacctt ccagactggt acctctagtc ccaagaatgc tactaaagtt      420
atcactctga accgtactgc ggatgggggtc tgggcttgta aatctaccca ggatccgatg     480
ttcactccga aaggttctga taac                                             504
```

<210> SEQ ID NO 20
<211> LENGTH: 168
<212> TYPE: PRT
<213> ORGANISM: Pseudomonas aeruginosa

<400> SEQUENCE: 20

```
Ala Leu Glu His His His His Gly Gly Gly Glu Ile Glu Ala
 1               5                  10                  15

Leu Lys Ala Glu Ile Glu Ala Leu Lys Ala Glu Ile Glu Ala Leu Lys
                20                  25                  30

Ala Glu Ile Glu Ala Leu Lys Ala Glu Ile Glu Ala Leu Lys Ala Gly
            35                  40                  45

Gly Gly Gly Glu Phe Ala Arg Ser Glu Gly Ala Ser Ala Leu Ala Thr
        50                  55                  60

Ile Asn Pro Leu Lys Thr Thr Val Glu Glu Ser Leu Ser Arg Gly Ile
65                  70                  75                  80

Ala Gly Ser Lys Ile Lys Ile Gly Thr Thr Ala Ser Thr Ala Thr Glu
                85                  90                  95

Thr Tyr Ala Gly Val Glu Pro Asp Ala Asn Lys Leu Gly Val Ile Ala
            100                 105                 110

Val Ala Ile Glu Asp Ser Gly Ala Gly Asp Ile Thr Phe Thr Phe Gln
        115                 120                 125

Thr Gly Thr Ser Ser Pro Lys Asn Ala Thr Lys Val Ile Thr Leu Asn
    130                 135                 140

Arg Thr Ala Asp Gly Val Trp Ala Cys Lys Ser Thr Gln Asp Pro Met
145                 150                 155                 160

Phe Thr Pro Lys Gly Ser Asp Asn
                165
```

<210> SEQ ID NO 21
<211> LENGTH: 504
<212> TYPE: DNA
<213> ORGANISM: Pseudomonas aeruginosa
<220> FEATURE:
<221> NAME/KEY: CDS
<222> LOCATION: (0)...(0)

<400> SEQUENCE: 21

```
gcgctcgagc accatcatca ccatggtggt ggtggcgagg tatccgcttt agagaaagaa      60
gtttctgctc tcgaaaaaga ggtcagtgct ctggaaaaag aggtgtcagc cttggaaaag     120
gaagtatcag cacttgagaa gggcggtgga ggagaattcg cgcgttcgga aggtgcttcg     180
gcgctggcga cgatcaaccc gctgaagacc actgttgaag agtcgctgtc gcgtggaatt     240
gctggtagca aaattaaaat tggtactact gcttctactg cgaccgaaac atatgccggc     300
gtcgagccgg atgccaacaa gttgggtgta attgctgtag caatcgaaga tagtggtgcg     360
ggtgatatta cctttacctt ccagactggt acctctagtc ccaagaatgc tactaaagtt     420
atcactctga accgtactgc ggatgggggtc tgggcttgta aatctaccca ggatccgatg    480
```

-continued

```
ttcactccga aaggttctga taac                                           504
```

<210> SEQ ID NO 22
<211> LENGTH: 168
<212> TYPE: PRT
<213> ORGANISM: Pseudomonas aeruginosa

<400> SEQUENCE: 22

```
Ala Leu Glu His His His His Gly Gly Gly Glu Val Ser Ala
 1               5                   10                  15

Leu Glu Lys Glu Val Ser Ala Leu Glu Lys Glu Val Ser Ala Leu Glu
            20                  25                  30

Lys Glu Val Ser Ala Leu Glu Lys Glu Val Ser Ala Leu Glu Lys Gly
            35                  40                  45

Gly Gly Gly Glu Phe Ala Arg Ser Glu Gly Ala Ser Ala Leu Ala Thr
50                      55                  60

Ile Asn Pro Leu Lys Thr Thr Val Glu Glu Ser Leu Ser Arg Gly Ile
65                  70                  75                  80

Ala Gly Ser Lys Ile Lys Ile Gly Thr Thr Ala Ser Thr Ala Thr Glu
                85                  90                  95

Thr Tyr Ala Gly Val Glu Pro Asp Ala Asn Lys Leu Gly Val Ile Ala
            100                 105                 110

Val Ala Ile Glu Asp Ser Gly Ala Gly Asp Ile Thr Phe Thr Phe Gln
            115                 120                 125

Thr Gly Thr Ser Ser Pro Lys Asn Ala Thr Lys Val Ile Thr Leu Asn
            130                 135                 140

Arg Thr Ala Asp Gly Val Trp Ala Cys Lys Ser Thr Gln Asp Pro Met
145                 150                 155                 160

Phe Thr Pro Lys Gly Ser Asp Asn
                165
```